(12) United States Patent
Oosawa

(10) Patent No.: US 7,620,229 B2
(45) Date of Patent: Nov. 17, 2009

(54) METHOD AND APPARATUS FOR AIDING IMAGE INTERPRETATION AND COMPUTER-READABLE RECORDING MEDIUM STORING PROGRAM THEREFOR

(75) Inventor: Akira Oosawa, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 656 days.

(21) Appl. No.: 10/917,520

(22) Filed: Aug. 13, 2004

(65) Prior Publication Data

US 2005/0105828 A1 May 19, 2005

(30) Foreign Application Priority Data

Aug. 14, 2003 (JP) ............................. 2003-293479

(51) Int. Cl.
G06K 9/00 (2006.01)
G06K 9/32 (2006.01)
(52) U.S. Cl. ........................ 382/130; 382/128; 382/131; 382/132; 382/294
(58) Field of Classification Search ......... 382/128–132, 382/294
See application file for complete search history.

(56) References Cited

U.S. PATENT DOCUMENTS

| | | | |
|---|---|---|---|
| 5,359,513 A | 10/1994 | Kano et al. | |
| 5,790,690 A | 8/1998 | Doi et al. | |
| 6,363,163 B1 * | 3/2002 | Xu et al. | 382/130 |
| 6,661,425 B1 * | 12/2003 | Hiroaki | 345/629 |
| 2001/0002934 A1 | 6/2001 | Oosawa | |
| 2001/0048757 A1 | 12/2001 | Oosawa | |
| 2002/0128547 A1 * | 9/2002 | Furuhashi et al. | 600/407 |
| 2004/0101177 A1 * | 5/2004 | Zahlmann et al. | 382/128 |
| 2004/0114790 A1 | 6/2004 | Yamamoto et al. | |

OTHER PUBLICATIONS

"Digital image subtraction of temporally sequential chest images for detection of interval change", by A. Kano, et al., Medical Physics, AAPM, vol. 21, Issue 3, Mar. 1994, pp. 453-461.*

* cited by examiner

Primary Examiner—John B Strege
(74) Attorney, Agent, or Firm—Sughrue Mion, PLLC

(57) ABSTRACT

In comparative image reading of projection images representing an observation target in two three-dimensional images of the same subject photographed at different times, alignment accuracy can be improved between the projection images and artifacts in subtraction images can be suppressed. In each of the three-dimensional images, pixels in a region specified by a cross section perpendicular to an observation direction and a thickness are projected, and the projection images are generated by repeating the procedure while moving a position of the cross section in the observation direction. Alignment processing and subtraction image generation is carried out between the corresponding projection images, and a superposed subtraction image is generated by superposing the generated subtraction images. Consequently, an effect of three-dimensional body movement of the subject at the time of photography can be suppressed than a projection image generated by projecting the entire observation target.

23 Claims, 18 Drawing Sheets

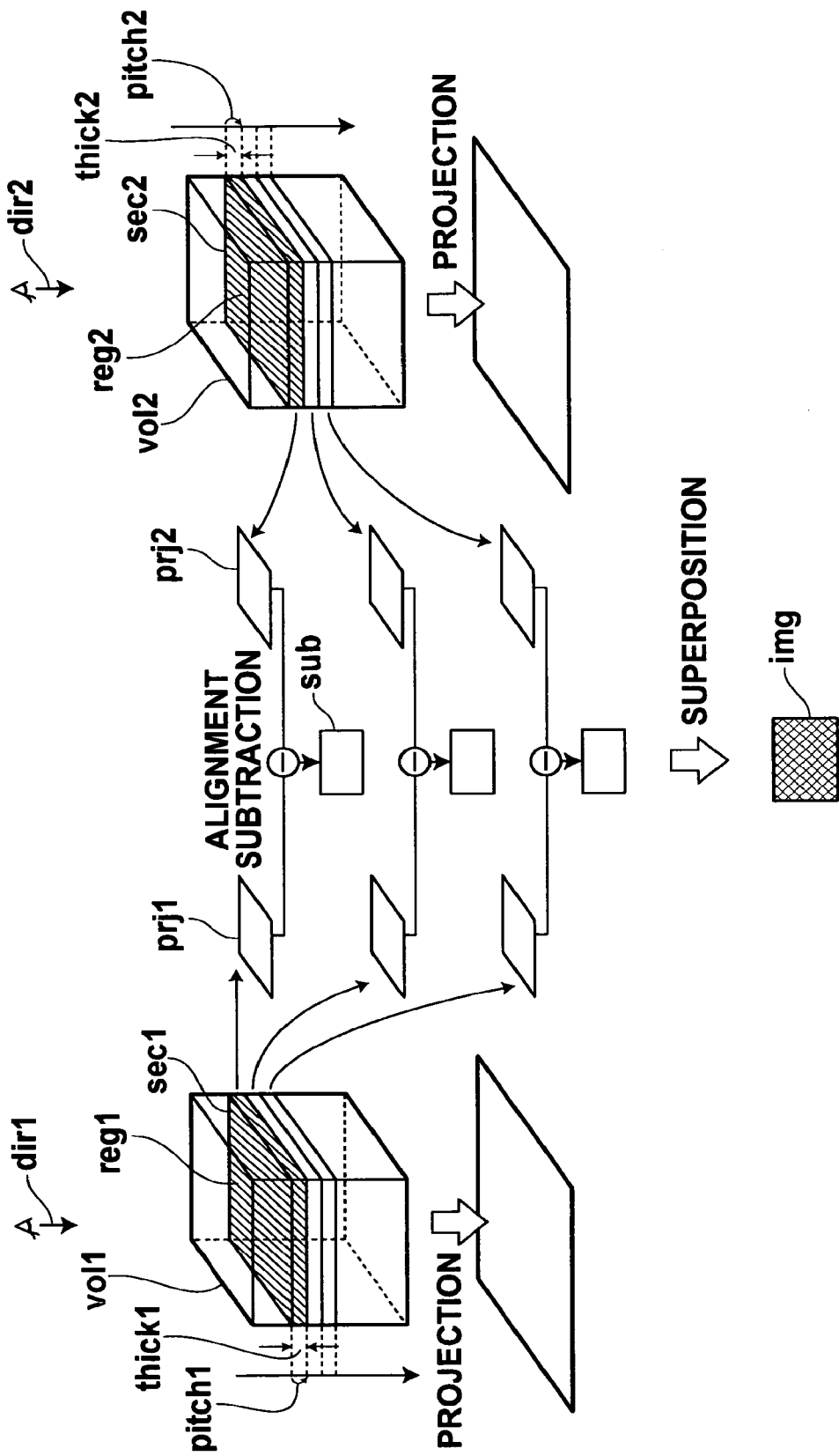

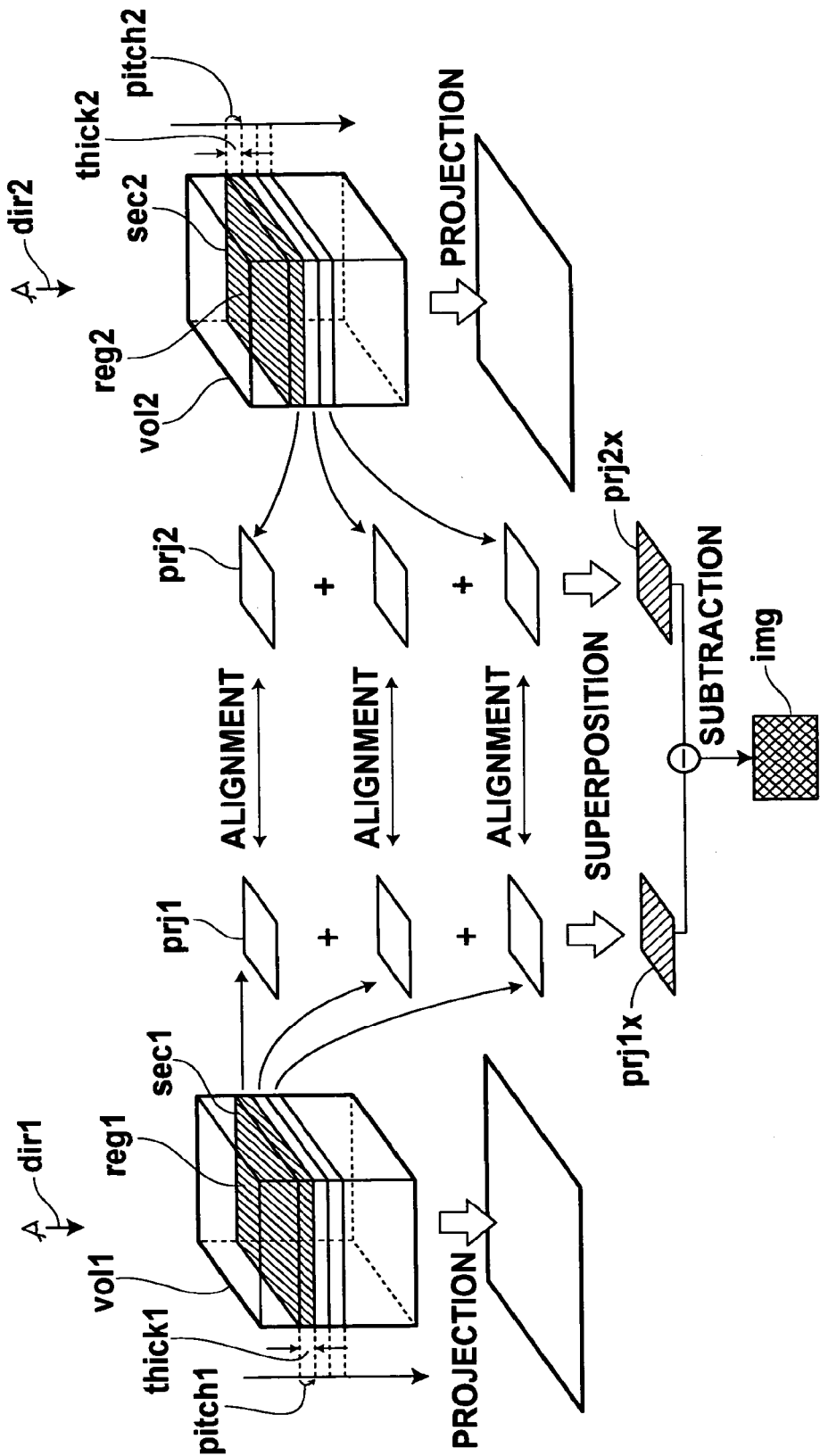

FIG.3A
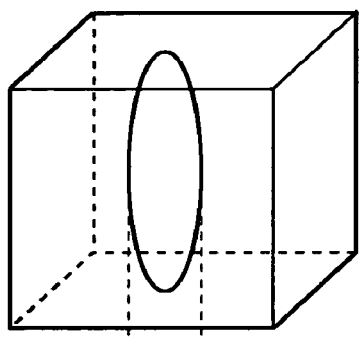
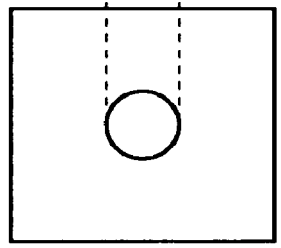
FIG.3B
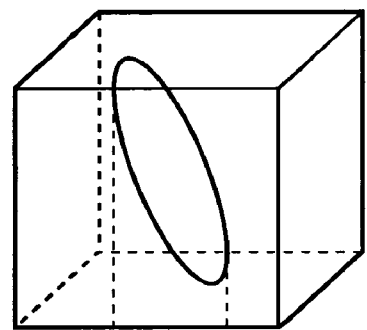
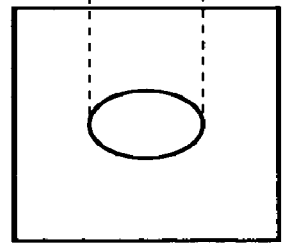

FIG.4A
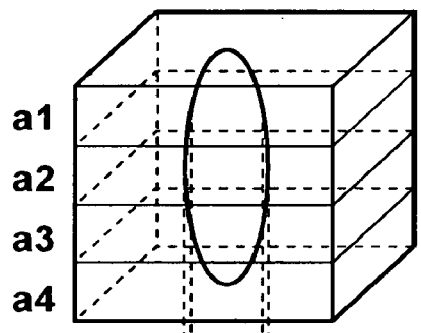
a1
a2
a3
a4
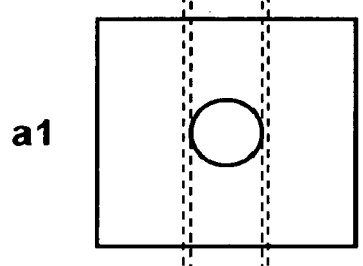
a1
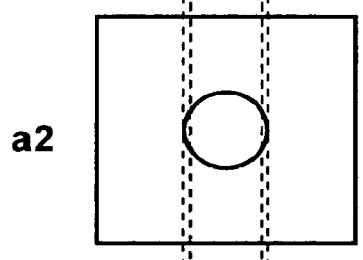
a2
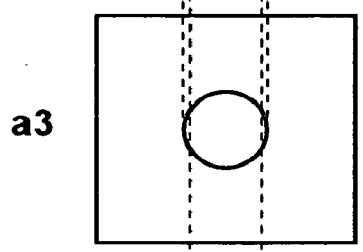
a3
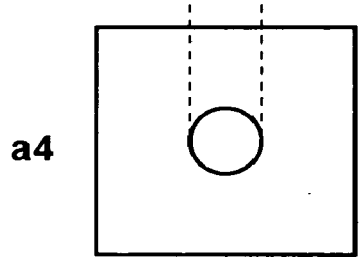
a4
FIG.4B
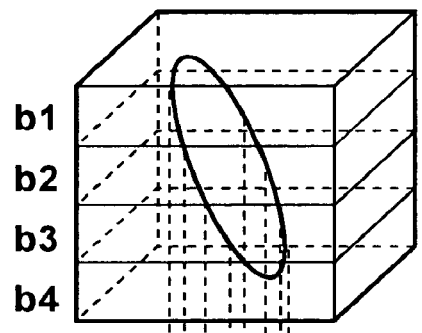
b1
b2
b3
b4
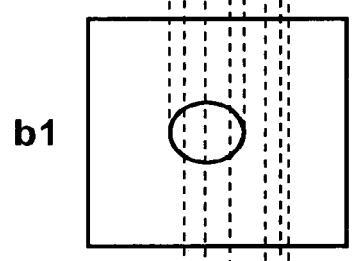
b1
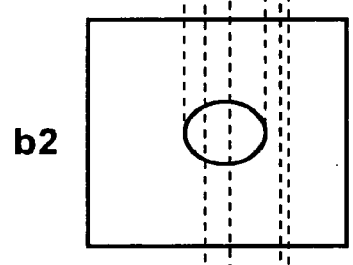
b2
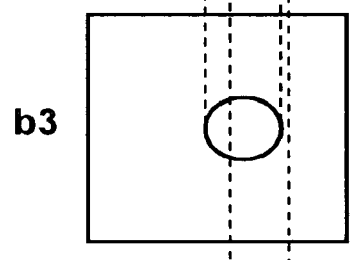
b3
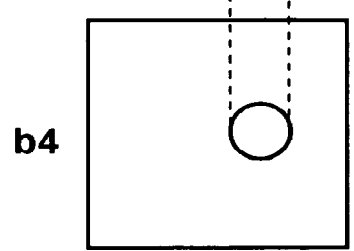
b4

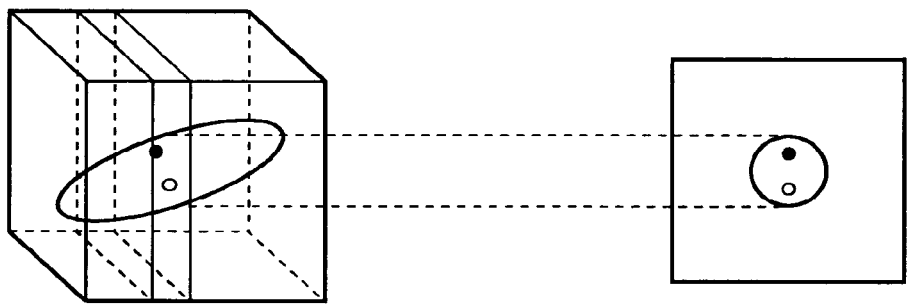
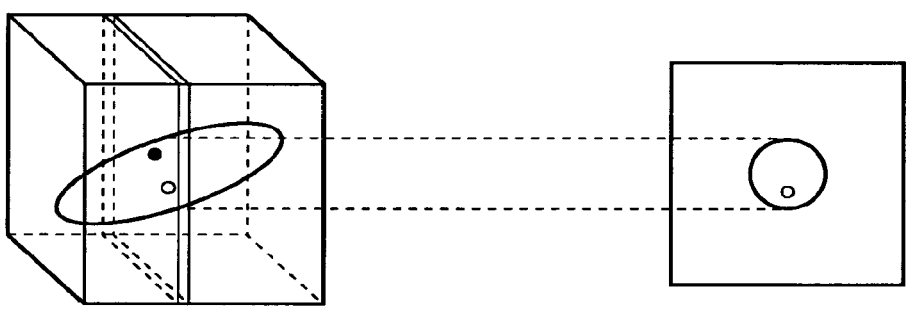
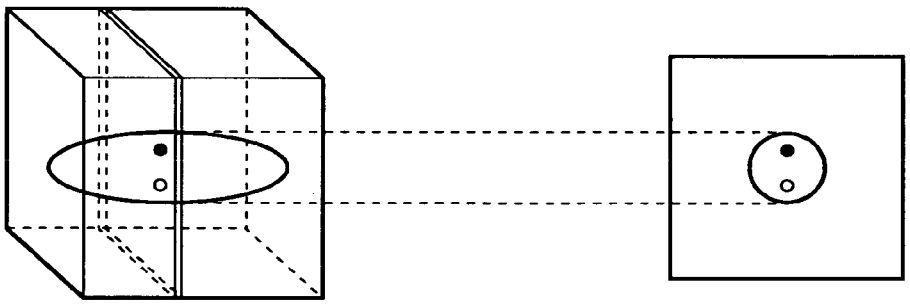

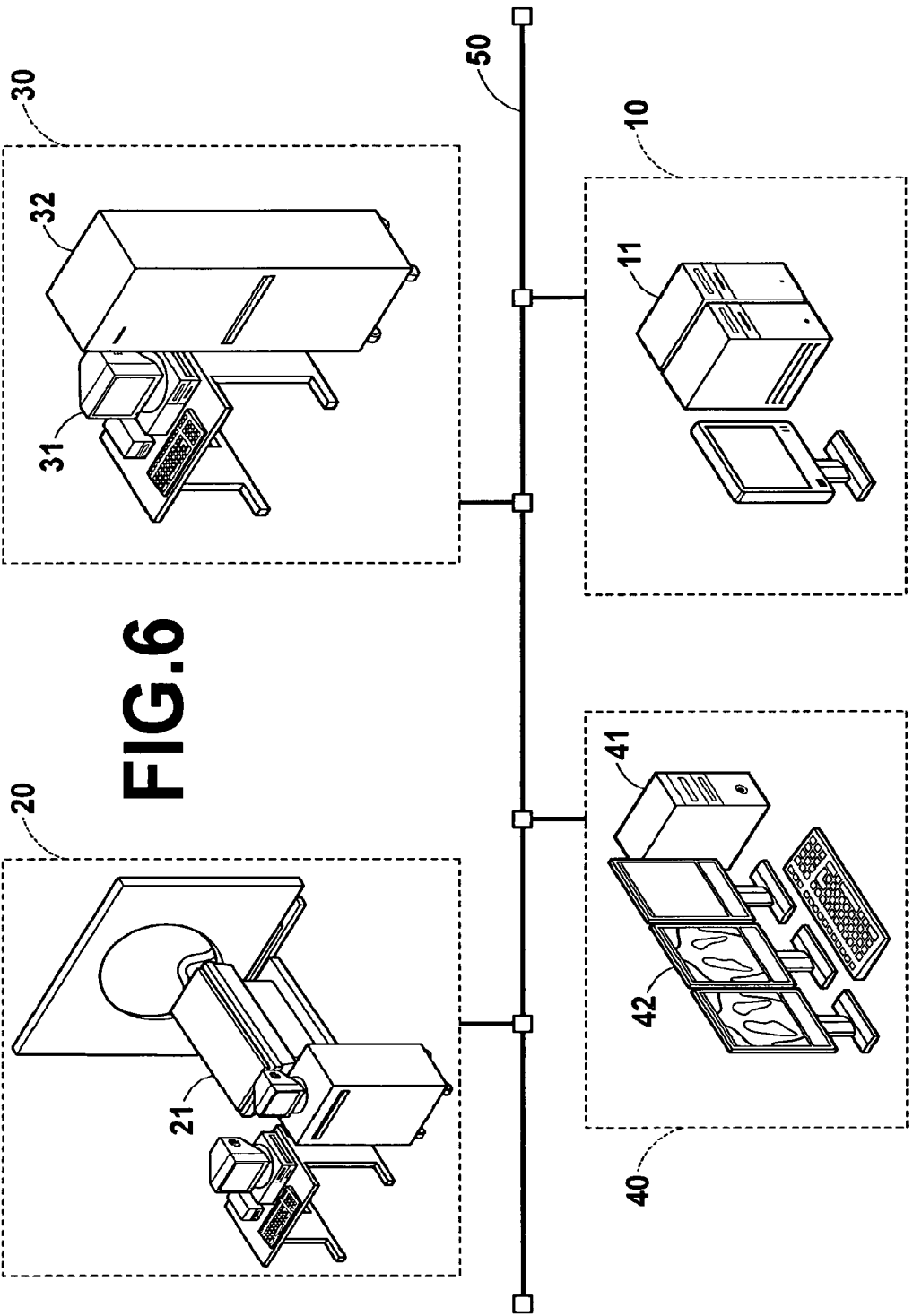

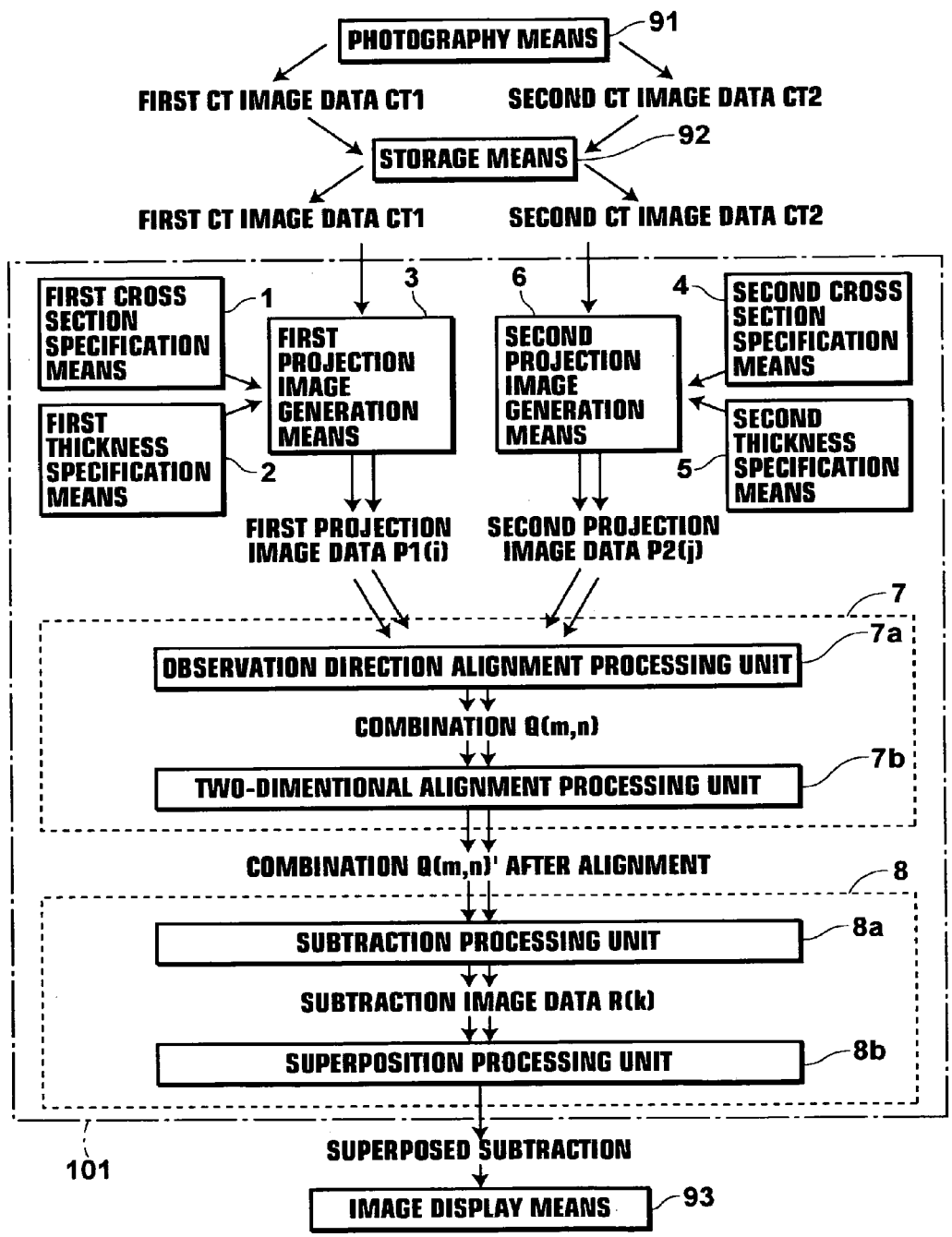

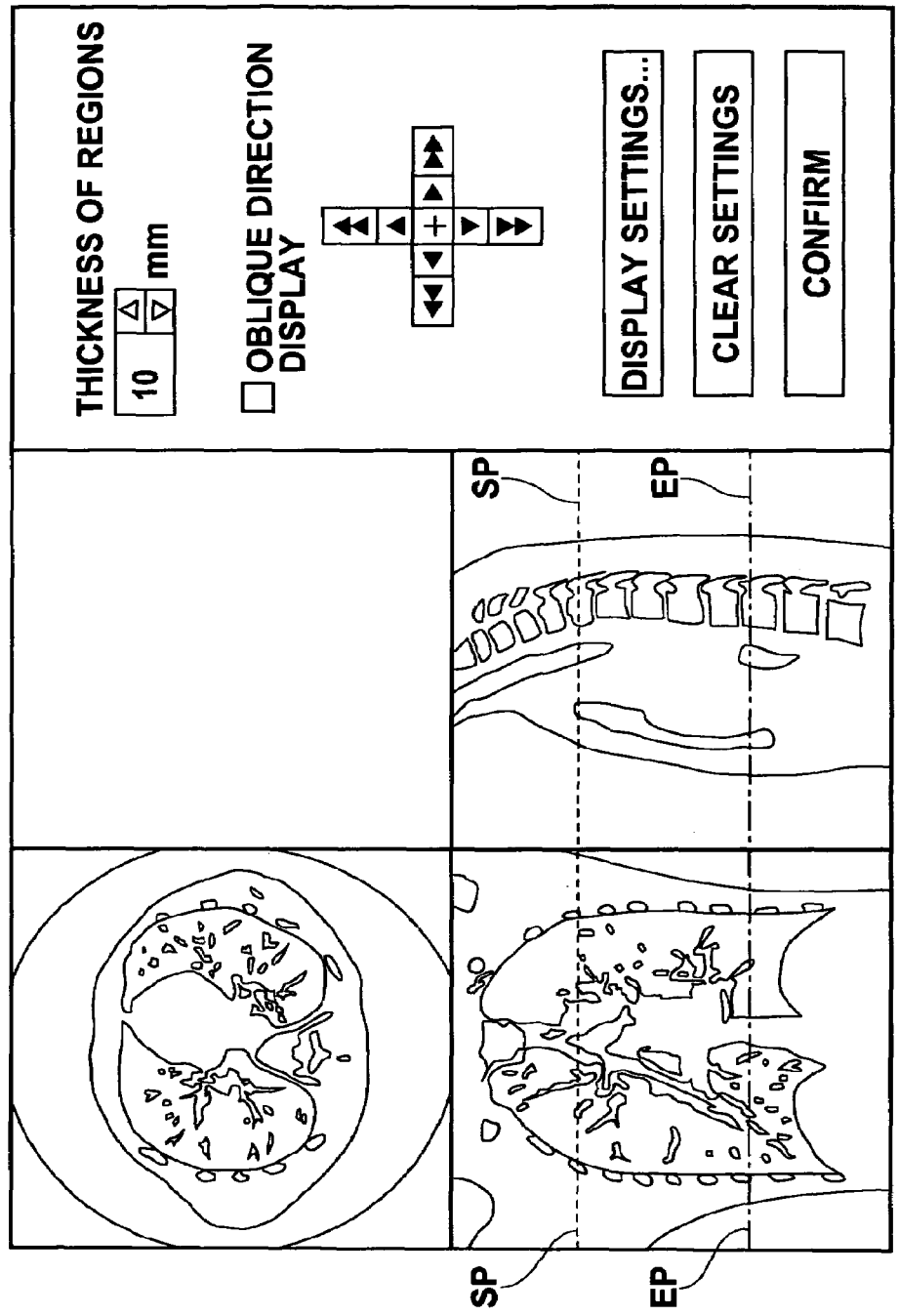

PAST IMAGE

CURRENT IMAGE

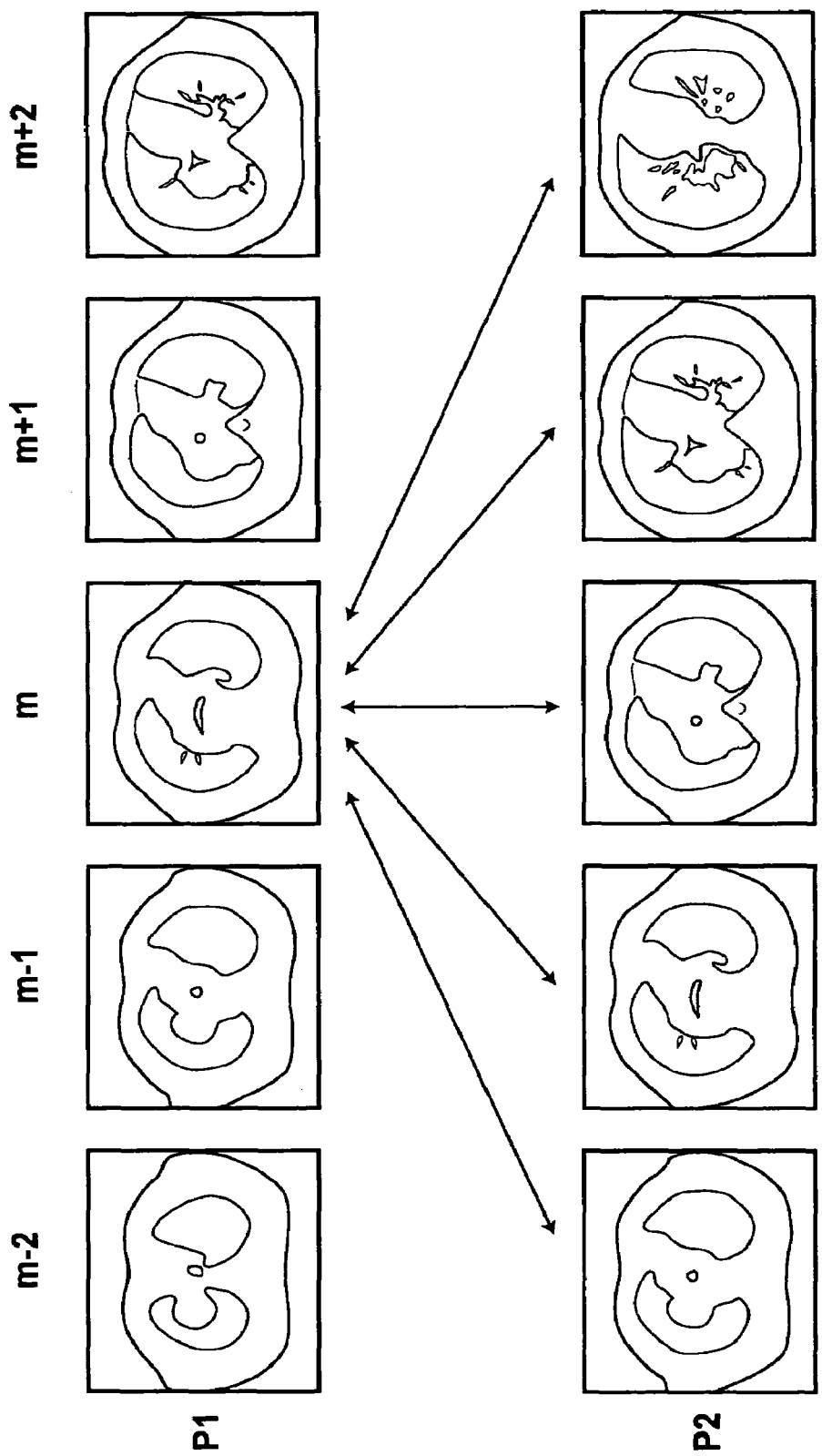

FIG.12
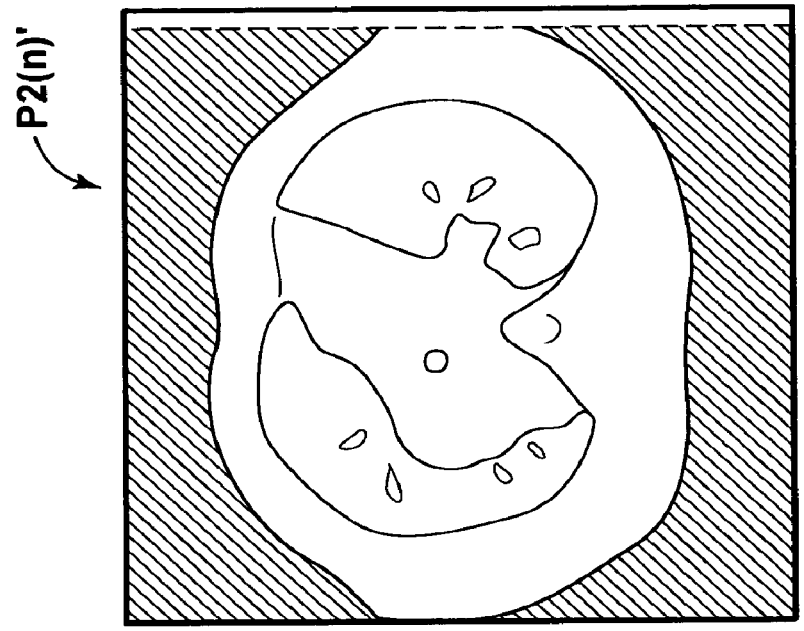
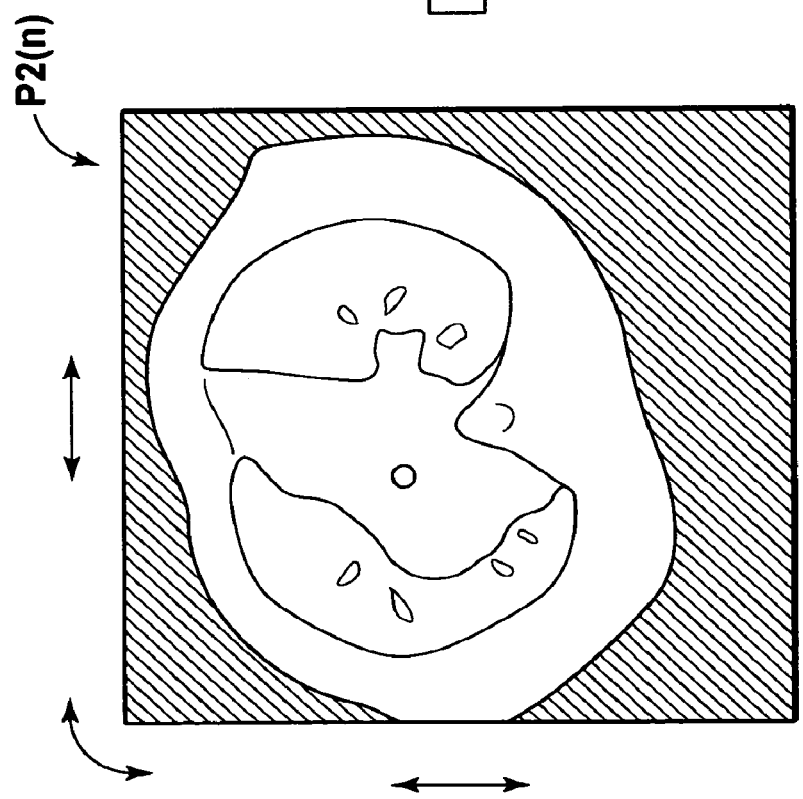

FIG.13
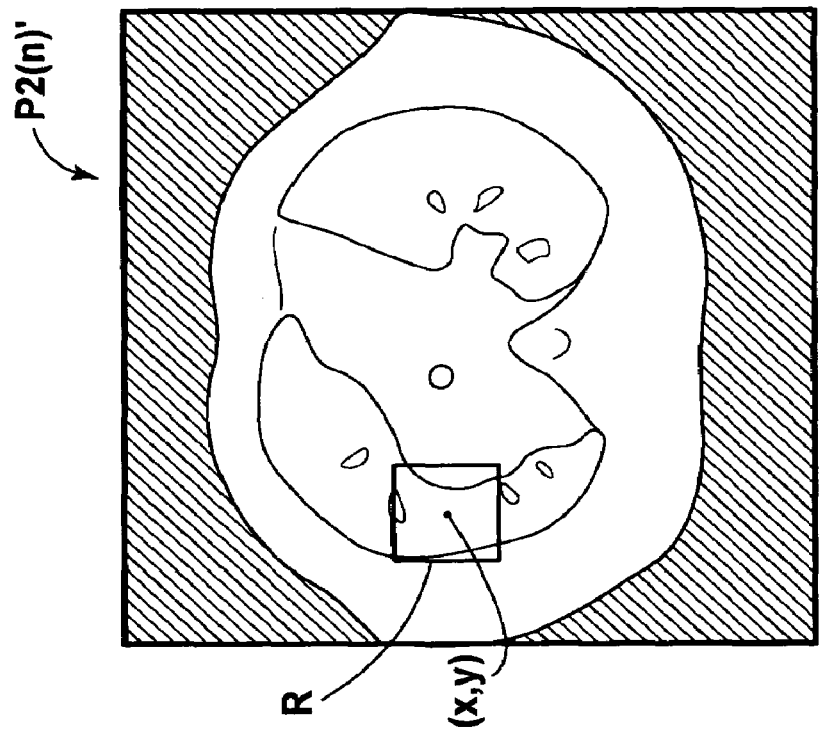
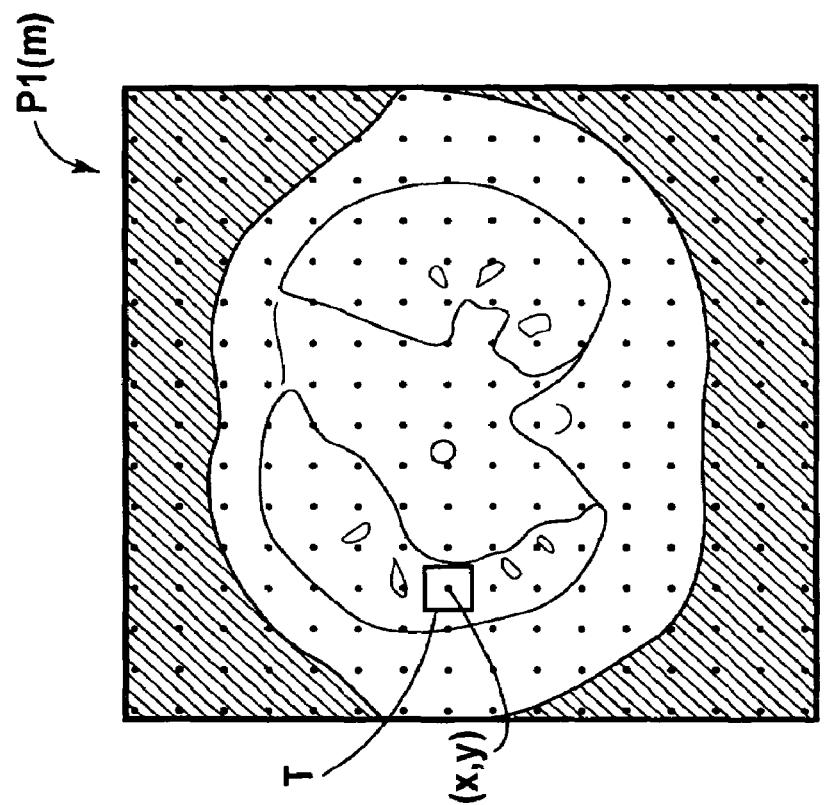

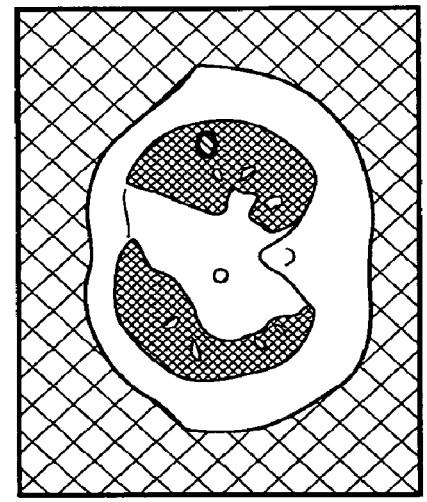
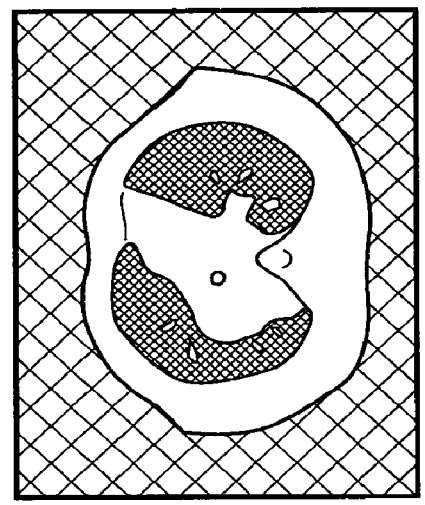
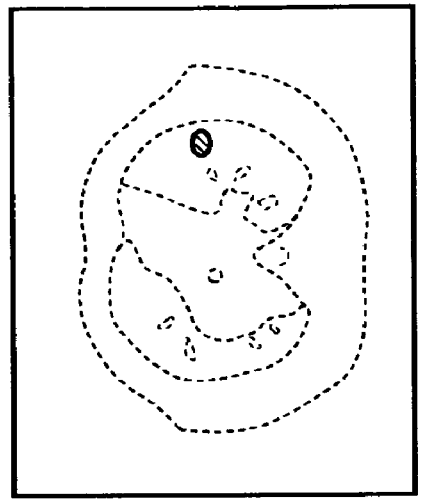
FIG.15A FIRST OBSERVATION TARGET IMAGE
FIG.15B SECOND OBSERVATION TARGET IMAGE
FIG.15C SUPERPOSED SUBTRACTION IMAGE

METHOD AND APPARATUS FOR AIDING IMAGE INTERPRETATION AND COMPUTER-READABLE RECORDING MEDIUM STORING PROGRAM THEREFOR

BACKGROUND OF THE INVENTION

1. Field of the Invention

The present invention relates to a method and an apparatus for aiding image interpretation, and to a computer-readable recording medium storing a program therefor. More specifically, the present invention relates to a method and an apparatus for aiding comparative image reading between two projection images by aligning projection images generated from two three-dimensional images representing the same subject photographed at different times, and to a computer-readable recording medium storing a program therefor.

2. Description of the Related Art

Inspection of a subject has been carried out in various fields, based on comparison of a difference between two or more images thereof. For example, in the field of manufacturing, an image of a product photographed at the time of production thereof is compared with an image thereof obtained after endurance tests thereon. A part showing a substantial difference is then detected as a part that needs to be improved in terms of endurance. In the field of medicine, a physician carries out comparative image reading on radiographs of a patient obtained at different times, and a plan of treatment can be discussed by understanding an interval change such as a progress or cure of a disease.

As a method of aiding such comparative image reading, a temporal subtraction method has been known. In a temporal subtraction method, an interval change is extracted and emphasized by generating a temporal subtraction image (hereinafter simply referred to as a subtraction image) through alignment of the same subject in images photographed at different times, with reference to a structural characteristic therein. More specifically, overall alignment processing (called global matching) is carried out for detecting an overall shift vector (a displacement vector) between two images. Thereafter, a shift vector for each of local regions in the images is detected and used for local alignment processing (called local matching) for determination of a shift vector for each of pixels. The subject in one of the two images is then aligned to the subject in the other image through non-linear transformation (called warping) on one of the images according to the shift vector. A subtraction image is then generated by subtraction processing on the warped image and the other image, which enables comparatively preferable alignment between the two images (see U.S. Pat. Nos. 5,359,513 and 5,790,690 and U.S. Patent Laid-Open Nos. 20010002934 and 20010048757 and "Digital image subtraction of temporally sequential chest images for detection of interval change", by A. Kano, K. Doi, H. MacMahon, D. Hassell, M. L. Giger, Medical Physics, AAPM, Vol. 21, Issue 3, March 1994, p. 453-461).

In the inventions described in U.S. Pat. Nos. 5,359,513 and 5,790,690 and U.S. Patent Laid-Open Nos. 20010002934 and 20010048757 and in the paper written by A. Kano et al., a temporal subtraction method is applied to simple X-ray images wherein a whole thickness of a subject viewed from a direction of photography is projected. However, application of a temporal subtraction method has also been proposed for cross-sectional CT images along axial planes (planes perpendicular to the axis of a human body), in addition to simple X-ray images (see U.S. Pat. No. 6,363,163, for example).

However, in the invention described in U.S. Pat. No. 6,363,163, temporal subtraction is carried out on cross-sectional images having a thickness substantially equal to the thickness of slices used at the time of photography. Therefore, an interval change to be observed does not necessarily exist in the cross-sectional images to be processed. Consequently, comparative image reading is necessary between the cross-sectional images of the respective slices having been subjected to the temporal subtraction, and a person who carries out diagnosis (hereinafter referred to as a diagnostician) is burdened with the comparative image reading, which is a time-consuming process. Furthermore, in the invention described in U.S. Pat. No. 6,363,163, the thickness of the cross-sectional images is 10 mm. However, based on a progress in a photography technique such as multi-slice CT and necessity of high resolution for direct image reading between cross-sectional images, photography using a thickness of several millimeters is preferred, which makes the above-described problem more apparent.

For this reason, application of a temporal subtraction method has been proposed to projection images wherein a whole thickness of a subject viewed from a direction of observation is projected, based on a three-dimensional chest CT image (see U.S. Patent Laid-Open No. 20040114790, for example). According to this method, an interval change of a subject to be observed can be detected by viewing only one subtraction image, and a burden on a diagnostician is expected to be reduced greatly.

However, in the invention described in U.S. Patent Laid-Open No. 20040114790, if a change in three-dimensional positioning of the body of a subject (such as forward or backward inclination or rotation of the body) or a state of the subject (such as different respiratory states in the case of photography of chest images) occurs between images to be subjected to comparative image reading, the change causes the same structural characteristic to be projected in different shapes. Therefore, accuracy of alignment is lowered, and artifacts are generated in a subtraction image. For example, in the case where a three-dimensional structure as a subject having an elongated elliptic shape stands up in a vertical direction at the time of photography of an image in FIG. 3A while the subject stands up with slight inclination at the time of photography of another image shown in FIG. 3B, if all pixels in the direction of thickness of the subject are projected, the subject is projected as a circular object for the image in FIG. 3A while the subject is projected as an elliptic object for the image in FIG. 3B. For this reason, the structural characteristic used as reference for alignment does not correlate well between the two images, leading to a decrease in alignment accuracy.

SUMMARY OF THE INVENTION

The present invention has been conceived based on consideration of the above circumstances. An object of the present invention is therefore to provide an image interpretation aiding method and an image interpretation aiding apparatus for improving alignment accuracy regarding an observation target between projection images representing the observation target in two three-dimensional images of the same subject photographed at different times, and for suppressing artifacts in a subtraction image. The present invention also provides a computer-readable recording medium storing a program therefor.

As shown in FIG. 1 or 2, an image interpretation aiding method of the present invention comprises the steps of:

generating first projection images (prj1) of a first region (reg1) in a first three-dimensional image (vol1) representing a subject by projecting, onto a plane perpendicular to a first observation direction (dir1) to the subject in the first three-dimensional image, pixels in the first region specified by a first cross section (sec1) perpendicular to the first observation direction and a first thickness (thick1) equal to a first pitch (pitch1), which is a thickness from the first cross section in the first observation direction, while moving a position of the first cross section in the first observation direction by the first pitch;

generating second projection images (prj2) of a second region (reg2) in a second three-dimensional image (vol2) representing the subject photographed at a time different from the first three-dimensional image by projecting, onto a plane perpendicular to a second observation direction to the subject in the second three-dimensional image, pixels in the second region specified by a second cross section (sec2) perpendicular to the second observation direction and a second thickness (thick2) equal to a second pitch (pitch2), which is a thickness from the second cross section in the second observation direction, while moving a position of the second cross section in the second observation direction by the second pitch;

carrying out alignment processing for aligning the subject in each of combinations of the first projection images and the second projection images corresponding to each other;

generating a superposed subtraction image (img) based on a difference in all the first projection images and all the second projection images having been subjected to the alignment processing.

More specifically, the superposed subtraction image is generated according to two manners of processing described below:

(1) As shown in FIG. 1, the superposed subtraction image (img) is generated by superposing subtraction images (sub) generated from a difference in each of the combinations of the first projection images and the corresponding second projection images having been subjected to the alignment processing.

(2) As shown in FIG. 2, a first superposed projection image (prj1x) is generated by superposing the first projection images having been subjected to the alignment processing while a second superposed projection image (prj2x) is generated by superposing the second projection images having been subjected to the alignment processing. The superposed subtraction image (img) is then generated by finding a difference between the first superposed projection image and the second superposed projection image.

An image interpretation aiding apparatus of the present invention is an apparatus for realizing the image interpretation aiding method of the present invention. The image interpretation aiding apparatus of the present invention comprises:

first cross section specification means for specifying a first cross section that is perpendicular to a first observation direction to a subject in a first three-dimensional image representing the subject;

first thickness specification means for specifying a first thickness from the first cross section in the first observation direction;

first projection image generation means for generating first projection images of a first region in the first three-dimensional image by projecting, onto a plane perpendicular to the first observation direction, pixels in the first region specified by the first cross section and the first thickness while moving a position of the first cross section in the first observation direction by a pitch equal to the first thickness;

second cross section specification means for specifying a second cross section perpendicular to a second observation direction to the same subject in a second three-dimensional image obtained at a time different from the first three-dimensional image;

second thickness specification means for specifying a second thickness from the second cross section in the second observation direction;

second projection image generation means for generating second projection images of a second region in the second three-dimensional image by projecting, onto a plane perpendicular to the second observation direction, pixels in the second region specified by the second cross section and the second thickness while moving a position of the second cross section in the second observation direction by a pitch equal to the second thickness;

alignment processing means for carrying out alignment processing on the subject in each of combinations of the first projection images and the second projection images corresponding to each other; and superposed subtraction image generation means for generating a superposed subtraction image based on a difference in all the first projection images and all the second projection images having been subjected to the alignment processing.

As an example of processing carried out by the superposed subtraction image generation means, the same processing as (1) and (2) described above may be listed (see FIGS. 1 and 2, respectively).

An image interpretation aiding program stored in a computer-readable recording medium of the present invention causes a computer to function as the image interpretation aiding apparatus described above. In other words, the image interpretation aiding program causes a computer to execute the above-described image interpretation aiding method. More specifically, the image interpretation aiding program causes a computer to function as:

first cross section specification means for specifying a first cross section that is perpendicular to a first observation direction to a subject in a first three-dimensional image representing the subject;

first thickness specification means for specifying a first thickness from the first cross section in the first observation direction;

first projection image generation means for generating first projection images of a first region in the first three-dimensional image by projecting, onto a plane perpendicular to the first observation direction, pixels in the first region specified by the first cross section and the first thickness while moving a position of the first cross section in the first observation direction by a pitch equal to the first thickness;

second cross section specification means for specifying a second cross section perpendicular to a second observation direction to the same subject in a second three-dimensional image obtained at a time different from the first three-dimensional image;

second thickness specification means for specifying a second thickness from the second cross section in the second observation direction;

second projection image generation means for generating second projection images of a second region in the second three-dimensional image by projecting, onto a plane perpendicular to the second observation direction, pixels in the second region specified by the second cross section and the second thickness while moving a position of the second cross section in the second observation direction by a pitch equal to the second thickness;

alignment processing means for carrying out alignment processing on the subject in each of combinations of the first projection images and the second projection images corresponding to each other; and superposed subtraction image generation means for generating a superposed subtraction image based on a difference in all the first projection images and all the second projection images having been subjected to the alignment processing.

As an example of processing carried out by the computer as the superposed subtraction image generation means, the same processing as (1) and (2) described above may be listed (see FIGS. 1 and 2, respectively).

The image interpretation aiding method and the image interpretation aiding apparatus of the present invention will be described next in detail.

As an example of the subject, a part of a human body such as the chest can be used.

The first (or second) three-dimensional image refers to an image based on image data wherein positions of pixels are defined in a three-dimensional space. More specifically, the first (or second) three-dimensional image refers to an image based on volume data or image data obtained by photography using CT (Computed Tomography) or MRI (Magnetic Resonance Imaging), for example.

In the case where the first and second three-dimensional images respectively comprise cross-sectional images representing slices formed by sequentially slicing the subject according to predetermined slice thicknesses as in the case of images based on CT or MRI, the first and second thicknesses are preferably thicker than the predetermined slice thicknesses of the first and second three-dimensional images, respectively. In this case, the predetermined slice thickness of the first three-dimensional image may be equal to or different from the predetermined slice thickness of the second three-dimensional image.

The first and second thickness specification means may allow a diagnostician to use an arbitrary value as the first and second thicknesses. Alternatively, the first and second thickness specification means may automatically use values that are predetermined by the image interpretation aiding apparatus of the present invention.

In the case where the first and second three-dimensional images respectively comprise cross-sectional images representing slices formed by sequentially slicing the subject according to predetermined slice thicknesses, the first and second thickness specification means may obtain the slice thicknesses of the first and second three-dimensional images, respectively. In this case, the first and second thickness specification means examine values of the first and second thicknesses set by a diagnostician with reference to the slice thicknesses that have been obtained so that the diagnostician can use only values greater than the first and second slice thicknesses, respectively. Alternatively, the first and second thickness specification means may automatically calculate the first and second thicknesses to respectively become greater than the first and second slice thicknesses, according to a predetermined calculation method based on the slice thicknesses that have been obtained. As a method of calculating the thicknesses, addition of a predetermined value to the slice thicknesses or multiplication of the slice thicknesses may be used, for example.

The first (or second) observation direction to the subject refers to a direction in which an observer observes the subject. Therefore, the observer observes cross sections perpendicular to the direction. The observation direction may be any direction. For example, in the case of CT images of a human chest, the observation direction may be an axial direction perpendicular to slices obtained by the photography. Alternatively, the observation direction may be a frontal direction perpendicular to the axial direction, or a side direction. In addition, the observation direction may be a direction that is not perpendicular to the axial direction, that is, an oblique direction.

The first observation direction may not necessarily be the same as the second observation direction. However, in terms of accuracy of the alignment processing that will be described later, it is preferable for the first observation direction to be close to the second observation direction. That is, it is preferable for the first observation direction to be substantially the same as the second observation direction. For example, in the case where the first and second three-dimensional images are obtained by photographing a human chest along the axial direction from the top (closer to the head) with a CT apparatus, the first and second observation directions may be directions expressed by the same vector in respective coordinate systems relative to the directions of photography of the three-dimensional images. However, in reality, three-dimensional positioning of the subject may be different between the first and second three-dimensional images at the time of photography. Therefore, the directions of photography do not exactly match the axial direction of the subject. Consequently, the first observation direction relative to the subject is not the same as the second observation direction. FIG. 9 shows the case where the first and second observation directions are the photography directions (the directions of z axes) of the first and second three-dimensional images, respectively. In the case shown in FIG. 9, the subject is inclined to the left at the time of photography of the second three-dimensional image, compared to the case of photography of the first three-dimensional image. Therefore, the first observation direction relative to the subject does not agree with the second observation direction.

For this reason, the following methods can be used to cause the first observation direction to substantially agree with the second observation direction:

(1) Photography is carried out to cause the photography direction of the first three-dimensional image to substantially agree with the photography direction of the second three-dimensional image.

(2) A diagnostician manually specifies the cross sections so as to cause the observation directions to be substantially the same, by using the first and second cross section specification means.

(3) A three-dimensional region of interest is set in either the first three-dimensional image or the second three-dimensional image, and the region is translated and rotated in the other three-dimensional image. Magnitude of displacement and rotation of the region is found when correlation of pixel values satisfies a predetermined reference value between the region in the former three-dimensional image and in a corresponding region in the latter three-dimensional image, and pixels in at least one of the three-dimensional images are rotated and translated according to the magnitude of displacement and rotation. In this manner, the two images are roughly aligned to each other, and a direction expressed by the same inclination (vector) in the respective coordinate systems for the two images after the alignment is used as the first and second observation directions.

The first and second thicknesses are not necessarily the same. However, in terms of alignment accuracy that will be described later, it is preferable for the two thicknesses to be substantially the same.

A range in which the first (or second) cross section is moved in the first (or second) observation direction is preferably a range including a part of the subject as an observation target. For example, in the case where the subject is a human chest and the first (or second) cross section is perpendicular to the axial direction of the body, the observation target refers to entire lung fields, or either the upper or lower lobes. By moving the first (or second) cross section, two or more regions are used as the first (or second) region.

As an example of projecting the pixels in the first (or second) region onto the plane perpendicular to the first (or second) observation direction, an average of pixel values in the first (or second) region may be found in the first (or second) observation direction. In order to find the average, the pixel values may be averaged at a plurality of positions of a line that penetrates the first (or second) region and is expressed by the same vector as the first (or second) observation direction. The pixel values along the line may be found by interpolation based on pixel values around the line.

Each of the combination of the first and second projection images corresponding to each other refers to a combination of the first and second projection images wherein positions of the first and second regions used for generating the projection images correspond to each other in the first and second observation directions to the subject. The first projection images may or may not have one-to-one correspondence with the second projection images. In addition, some of either the first or second projection images may not have the counterparts. Since the number of the regions used as the first region is two or larger, and so is the number of the regions used as the second region, the number of the combinations also becomes two or larger.

It is preferable for the alignment processing to find a shift vector for each of the pixels in one of the images to the other image by finding correspondence between the pixels with reference to a structural characteristic in the two images. More specifically, overall linear alignment processing (called global matching) is carried out for detecting an overall shift vector between the two images as has been described in the temporal subtraction method in U.S. Pat. Nos. 5,359,513 and 5,790,690 and U.S. Patent Laid-Open Nos. 20010002934 and 20010048757 and a shift vector for each of local regions in the two images is found thereafter. Local non-linear alignment processing (called local matching) is then carried out for finding the shift vector for each of the pixels according to the shift vector for each of the local regions. Non-linear transformation (called warping) is thereafter carried out on one of the images, for alignment based on the shift vector for each of the pixels. The method of alignment may be a combination of linear and non-linear transformations, or either linear or non-linear transformation alone.

As an example of processing to find the difference, subtraction may be carried out between the pixels corresponding to each other in the two images so that an image based on the difference may be generated.

As an example of processing for superposing, simple averaging may be carried out on the images to be processed. Before the superposing, it is preferable for alignment processing to be carried out on the images to be processed, with reference to the structural characteristic therein. Processing for emphasizing the difference may also be carried out.

According to the image interpretation aiding method, the image interpretation aiding apparatus, and the program of the present invention, the first and second projection images are generated regarding the first and second three-dimensional images representing the same subject photographed at different times, by projecting the pixels in the regions specified by the predetermined cross sections and the predetermined thicknesses. For each of the combinations of the first and second projection images corresponding to each other, the alignment processing is carried out, and the superposed subtraction image is generated based on the difference between all the first projection images and all the second projection images having been subjected to the alignment processing. Therefore, alignment accuracy can be improved for the part as the observation target in the subject, and artifacts in the superposed subtraction image can be suppressed. Consequently, an observer can carry out comparative image reading with high accuracy, and the comparative image reading can also be carried out efficiently.

In the case where three-dimensional positioning or a state of the subject has changed between photography of the two three-dimensional images, the structural characteristic used as reference for alignment does not correlate well between the two images if the projection images are generated for regions including the entire observation target. Therefore, alignment accuracy is lowered. In the present invention on the other hand, if the projection images are generated by projecting the regions respectively including parts of the observation target, an effect of the change in positioning or the state of the subject in the projection images can be weakened than in projection images generated by projecting the entire observation target. Therefore, the structural characteristic used as alignment reference can correlate well, and alignment accuracy improves. For example, in the case where an observation target stands up vertically and with slight inclination as shown in FIG. 3, if projection images are generated by respectively projecting regions including the entire observation target, shapes of the observation target become different in the two projection images due to the inclination. Therefore, a structural characteristic does not correlate well in the two images, which leads to reduction in alignment accuracy. On the other hand, even in the case where the observation target is inclined, if projection images are generated by using four regions respectively including parts of the observation target as shown in FIG. 4, a difference in shapes of the observation target in the projection images is not larger than in the case shown in FIG. 3. Consequently, the structural characteristic used as reference for alignment can correlate well in the first and second projection images corresponding to each other. As a result, alignment can be carried out with higher accuracy, and artifacts can be suppressed in subtraction images generated from differences in each of combinations of the two projection images having been subjected to the alignment with high accuracy. Therefore, although a superposed subtraction image generated by superposing the subtraction images represents the same content as a subtraction image generated from the projection images in FIGS. 3A and 3B, the superposed subtraction image has fewer artifacts than the subtraction image generated by the projection images shown in FIGS. 3A and 3B, since the artifacts in the subtraction images have been suppressed before superposition. Although the case where the inclination of the observation target is different has been described above, the same effect can be obtained in other cases, such as the case where sizes of lung fields are different between two three-dimensional images obtained by photography of a human chest due to differences in respiratory states.

In the case where the first and second three-dimensional images respectively comprise a plurality of cross-sectional images representing slice regions formed by sequentially slicing a subject according to predetermined slice thicknesses and the first and second thicknesses are larger than the corresponding predetermined slice thicknesses of the three-dimensional images, alignment accuracy can be improved more than in the case where alignment processing is carried out on projection images generated by projection of regions having thicknesses equal to or smaller than the slice thicknesses.

This effect is explained in FIG. 5 where attention needs to be paid to two structural characteristics marked by ○ and ● in the observation targets shown in FIGS. 3 and 4. In FIG. 5A is shown the case where a projection image is generated by projecting a region having a thickness corresponding to a slice thickness of a three-dimensional image wherein the observation target stands vertically. In the case in FIG. 5A, the structural characteristics represented by ○ and ● are included in the projection image. In FIG. 5B is shown the case where a projection image is generated by projecting a region having the thickness corresponding to the slice thickness in a three-dimensional image wherein the observation target stands with slight inclination. Due to the inclination of the observation target, the two structural characteristics represented by ○ and ● are also inclined. Therefore, if a position of a cross section is specified in such a manner that the projection image includes a part shown by ○, for example, a part shown by ● may not be projected in some cases. Consequently, the number of corresponding structural characteristics that can be used as alignment reference between the projection images is reduced, and alignment accuracy is thus lowered. Meanwhile, as shown in FIG. 5C, if a region having a thickness thicker than the slice thickness is used for projection even in the case where the observation target has slight inclination, probability of inclusion of both the structural characteristics becomes higher, and reduction in the number of corresponding structural characteristics that can be used as alignment reference can be suppressed. In this manner, alignment accuracy can be improved.

In the case where the chest of a human body as the subject has an inclination difference of 5 degrees between the first and second three-dimensional images, for example, the observation target may shift by several to 10 mm in the observation direction due to the inclination difference. Meanwhile, a slice thickness is usually 0.5 to 8 mm in such photography. Therefore, if projection images are generated by projection of regions having the thicknesses corresponding to the slice thicknesses as shown in FIGS. 5A and 5B, the problem described above may occur. Furthermore, in consideration of the shape difference in the observation target as shown in FIG. 3, it is preferable for the first and second thicknesses to be larger than 10 mm, ideally, approximately 20 mm.

In the case where each of the three-dimensional images comprises cross sectional images representing slices of the subject, if alignment is carried out on projection images generated by projection of regions specified by a cross section and a thickness in an observation direction different from a photography direction, the relationship described above does not seem to exist between the slice thickness and the thickness of the regions used for generating the projection images. However, an upper limit of resolution of such a three-dimensional image is defined by the slice thickness, and interpolation is carried out between pixel values at the time of generation of the projection images. Therefore, a resolution of the projection images to be generated is indirectly defined by the slice thickness. Consequently, even in the case where the projection images are generated by projecting the region specified by the cross section and the thickness viewed from the observation direction different from the photography direction, the same effect can be obtained as in the case of generating the projection images by projection of the region specified by the cross section and the thickness in the observation direction that is the same as the photography direction if the first and second thicknesses are larger than the slice thicknesses.

In the case where the superposed subtraction image is generated by the difference between the first and second superposed projection images generated respectively through superposition of the first projection images and the second projection images after the alignment processing, alignment accuracy becomes higher not only for the superposed subtraction image but also for the first and second superposed projection images. Consequently, efficiency and accuracy of comparative image reading can be improved further by providing the superposed images.

Note that the program of the present invention may be procided being recorded on a computer readable medium. Those who are skilled in the art would know that computer readable media are not limited to any specific type of device, and include, but are not limited to: floppy disks, CD's, RAM's, ROM's, hard disks, magnetic tapes, and internet downloads, in which computer instructions can be stored and/or transmitted. Transmission of the computer instructions through a network or through wireless transmission means is also within the scope of this invention. Additionally, computer instructions include, but are not limited to: source, object, and executable code, and can be in any language, including higher level languages, assembly language, and machine language.

BRIEF DESCRIPTION OF THE DRAWINGS

FIG. 1 is a diagram showing how a superposed subtraction image is generated from two three-dimensional images according to a first method of the present invention;

FIG. 2 is a diagram showing how a superposed subtraction image is generated from two three-dimensional images according to a second method of the present invention;

FIGS. 3A and 3B respectively show cases where a three-dimensional structure standing upright and with slight inclination is projected onto a horizontal plane;

FIGS. 4A and 4B respectively show cases where four regions including parts of a three-dimensional structure standing upright and with slight inclination are projected onto a horizontal plane;

FIG. 5A shows a case where structural characteristics of a three-dimensional structure standing upright are projected onto a horizontal plane for a thickness equal to a slice thickness, FIG. 5B shows a case where the same structural characteristics of the three-dimensional structure standing with slight inclination are projected onto a horizontal plane for the thickness equal to the slice thickness, FIG. 5C shows a case where the same structural characteristics of the three-dimensional structure standing with the slight inclination are projected onto a horizontal plane for a thickness thicker than the slice thickness;

FIG. 6 is an illustration showing the configuration of a chest image diagnosis aiding system in embodiments of the present invention;

FIG. 7 is a block diagram showing the configuration of an image interpretation aiding apparatus and peripheral systems and flows of data in a first embodiment of the present invention;

FIG. 8 shows an example of a screen wherein first and second cross sections and first and second thicknesses are specified;

FIG. 10 shows alignment processing carried out by an observation direction alignment processing unit;

FIG. 12 shows global matching processing carried out by the two-dimensional alignment processing unit;

FIG. 13 shows local matching processing carried out by the two-dimensional alignment processing unit;

FIGS. 15A to 15C respectively show examples of a first observation target image, a second observation target image, and a superposed subtraction image displayed by image display means;

DESCRIPTION OF THE PREFERRED EMBODIMENTS

Figure 9B:
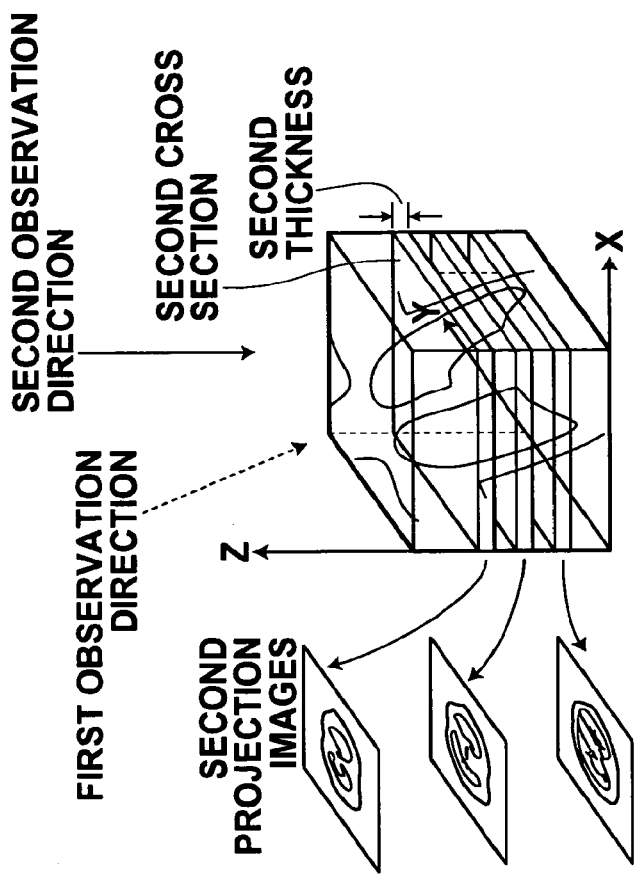
FIGS. 9A and 9B are illustrations for explaining processing to generate first and second projection images in the case where disagreement is observed between first and second observation directions.

Hereinafter, embodiments of the present invention will be described with reference to the accompanying drawings in the case where an interval change is observed based on CT images having the chest of a patient as a subject.

FIG. 6 shows the configuration of a chest image diagnosis aiding system including an image interpretation aiding apparatus 101 or 102 as an embodiment of the present invention. As shown in FIG. 6, an image photography/reading system 20, an image management system 30, an image interpretation aiding system 10, and an image display system 40 are connected in a communicable state via a network 50 such as a LAN.

The image photography/reading system 20 photographs and obtains images representing the subject, and includes a CT apparatus 21 for obtaining the CT images having the chest of the patient as the subject. The image photography/reading system 20 may include an MRI apparatus, (not shown) depending on a body part to be diagnosed.

The image interpretation aiding system 10 carries out image processing on the images photographed by the image photography/reading system 20, and generates images appropriate for image reading by a diagnostician. The image interpretation aiding system 10 includes an image processing server 11.

The image management system 30 stores and manages the images generated by the image photography/reading system 20 and the image interpretation aiding system 10, and comprises an image management server 31, a large-capacity external storage 32, and software for managing a database (such as an object relational database known as ORDB).

The image display system 40 displays the images generated by the image photography/reading system 20 and the image interpretation aiding system 10, and comprises a client PC 41 and three high-definition liquid crystal display devices 42 (hereinafter referred to as the high-definition LCD devices 42).

The image interpretation aiding apparatus 101 of a first embodiment of the present invention generates projection images by projecting pixels in regions specified by cross sections and thicknesses in two CT images representing the same subject but photographed at different times. The image interpretation aiding apparatus 101 then aligns lung fields in the projection images corresponding to each other, and generates subtraction images. The image interpretation aiding apparatus 101 further generates a superposed subtraction image by superposing the subtraction images. (In the explanation below, an image represented by an image data set has the same reference number as the image data set. For example, an image represented by an image data set Y1 is referred to as an image Y1).

FIG. 7 is a block diagram showing the configuration of the image interpretation aiding apparatus 101 and peripheral systems, and flows of data. As shown in FIG. 7, the image interpretation aiding apparatus 101 comprises:

(1) first cross section specification means 1 for specifying a first cross section perpendicular to a first observation direction to the subject in an image represented by a first CT image data set CT1 photographed by photography means 91;

(2) first thickness specification means 2 for specifying a first thickness from the first cross section in the first observation direction;

(3) first projection image generation means 3 for reading the first CT image data set CT1 from storage means 92, for generating first projection images of a first region in the first CT image CT1 by projecting pixels in the first region specified by the first cross section and the first thickness onto a plane perpendicular to the first observation direction while moving a position of the first cross section by a pitch equal to the first thickness in the first observation direction, and for outputting first projection image data sets P1(i);

(4) second cross section specification means 4 for specifying a second cross section perpendicular to a second observation direction to the subject in an image represented by a second CT image data set CT2 obtained by the photography means 91 before the first CT image CT1;

(5) second thickness specification means 5 for specifying a second thickness from the second cross section in the second observation direction;

(6) second projection image generation means 6 for reading the second CT image data set CT2 from the storage means 92, for generating second projection images of a second region in the second CT image CT2 by projecting pixels in the second region specified by the second cross section and the second thickness onto a plane perpendicular to the second observation direction while moving a position of the second cross section by a pitch equal to the second thickness in the second observation direction, and for outputting second projection image data sets P2(j);

(7) alignment processing means 7 for carrying out alignment processing on the subject in each combination Q(m,n) of an image represented by one of the first projection image data sets (hereinafter referred to as the first projection image data set P1(m)) and an image represented by one of the second projection image data sets (hereinafter referred to as the second projection image data set P2(n)) corresponding to the first projection image data set P1(m);

(8) superposed subtraction image generation means 8 for generating a superposed subtraction image based on a difference between all the first projection image sets P1(i) and all the second projection image sets having been subjected to the alignment processing (hereinafter referred to as aligned second projection images P2(j)"), and for outputting a superposed subtraction image data set S.

The alignment processing means 7 comprises an observation direction alignment processing unit 7a for selecting the combination Q(m,n) of the image P1(m) represented by the first projection image data set P1(m) and the image P2(n) represented by the second projection image P2(n) wherein positions of a structural characteristic correspond to each other in the observation directions to the subject, and a two-dimensional alignment processing unit 7b for aligning two-dimensional positions of the subject in the two projection images forming the combination Q(m,n). Note that m and n are reference numerals that denote each of the first and second projection images.

The superposed subtraction image generation means 8 comprises a subtraction processing unit 8a and a superposition processing unit 8b. The subtraction processing unit 8a generates a subtraction image based on a difference in each combination Q(m,n)' of the first projection image set P1(m) and the second projection image set that corresponds to the first projection image data set P1(m) and has been subjected to the alignment processing (hereinafter referred to as an aligned second projection image data set P2(n)"), and outputs subtraction image data sets R(k). The superposition processing unit 8b generates the superposed subtraction image by superposing the images represented by the subtraction image data sets R(k), and outputs the superposed subtraction image data set S.

The first projection image generation means 3, the second projection image generation means 6, the alignment processing means 7, and the superposed subtraction image generation means 8 are installed in the image processing server 11 of the image interpretation aiding system 10, and comprise programs executable by the image processing server 11, a main storage for storing data and instructions used by a CPU of the image processing server 11 and the programs, frame memories for image storage, an external storage such as a hard disc, interfaces for input/output and communication, and an operating system.

The first cross section specification means 1, the first thickness specification means 2, the second cross section specification means 4, and the second thickness specification means 5 are installed in the client PC 41, and comprise programs executable by the client PC 41, a main storage for storing data and instructions used by a CPU of the client PC 41 and the programs, interfaces for input/output and communication, and an operating system.

The photography means 91 is installed as the CT apparatus 21 of the image photography/reading system 20.

The storage means 92 is installed in the image management system 30, and comprises a program executable by the image management server 31, a main storage for storing data and instructions used by a CPU of the image management server 31 and the program, the large-capacity external storage 32 for storing the image data sets in relation to accompanying information such as the patient ID and the time and date of photography, interfaces for input/output and communication, the database management software, and an operating system.

The image display means 93 is installed in the image display system 40, and comprises a program executable by the client PC 41, a main storage for storing data and instructions used by the CPU of the client PC 41 and the program, frame memories for storing images to be displayed, an external storage such as a hard disc for storing the images, the high-definition LCD devices 42 for displaying the images, interfaces for input/output and communication, and an operating system.

A procedure carried out in the image interpretation aiding apparatus 101 and the peripheral systems will be described next. The first CT image CT1 and the second CT image CT2 have been photographed and obtained by the photography means 91, and transferred from the image photography/reading system 20 to the image management server 31 in the image management system 30 via the network 50 as the first CT image data set CT1 and the second CT image data set CT2 in relation to the accompanying information including the patient ID, the time and date of photography, a body part that has been photographed, and a slice thickness. The storage means 92 stores the first and second CT image data sets CT1 and CT2 in the large-capacity external storage 32 in relation to the accompanying information, according to a data structure and a data format defined by the database management software. The first and second CT images CT1 and CT2 can be searched for according to a search key using all or a part of the accompanying information.

The diagnostician who carries out comparative image reading selects a desired one of diagnostic manus (comparative image reading of CT images, in this case) in a menu screen displayed first on the client PC 41.

The client PC 41 sequentially displays screens for prompting the diagnostician to input or select information necessary for processing in accordance with the selected menu.

The diagnostician inputs the patient ID for identifying the patient to be diagnosed. The client PC 41 sends a search request for the accompanying information of the patient whose ID has been input to the image management server 31 through the network 50 via the image processing server 11. The image management server 31 searches the database based on the patient ID that has been received, and obtains a list of the accompanying information of the patient. The image management server 31 then sends the list to the client PC 41 through the network 50 via the image processing server 11.

The client PC 41 displays the list, and prompts the diagnostician to select the images used for diagnosis. The diagnostician selects the images used for the comparative image reading, that is, the CT images CT1 and CT2 from the displayed list regarding the patient. The client PC 41 sends information (such as the patient ID, the time and date of photography, and the body part) to identify the CT images CT1 and CT2 that have been selected to the image management server 31 through the network 50 via the image processing server 11. The image management server 31 searches the database according to the information that has been received, and obtains the CT image data sets CT1 and CT2. The image management server 31 sends the CT image data sets CT1 and CT2 to the image processing server 11 through the network 50. The image processing server 11 generates images wherein an entire thickness of the subject is projected in an axial direction, a frontal direction, and a side direction by using an MPR (MultiPlaner Reconstruction) method (see Japanese Unexamined Patent publication No. 2002-11000, for example) based on each of the CT image data sets CT1 and CT2, and sends image data sets representing the images to the client PC 41 through the network 50.

The client PC 41 receives the image data sets generated from the CT image data sets CT1 and CT2, and displays the three images (viewed from the axial, frontal, and side directions) represented by the image data sets generated from the first CT image data set CT1 on one of the high-definition LCD devices 42. FIG. 8 shows an example of a screen having the three images. The first cross section specification means 1 and the first thickness specification means 2 prompt the diagnostician to specify the cross section, a range in which the cross section moves, and the thickness.

The diagnostician sets a starting position SP and an ending position EP that is parallel to the starting position in the displayed image in order to include a part of the subject as an observation target, by using a mouse or the like of the client PC 41. Based on the starting position SP and the ending position EP, the first cross section specification means 1 specifies three-dimensional inclination of the first cross section (that is, the first observation direction perpendicular to the first cross section) in the first region in a three-dimensional space relative to a photography direction, and the range in which the first cross section moves in the first observation direction.

The diagnostician also inputs a value of thickness of the regions in a box in the right of the screen, by using a keyboard or the mouse. The first thickness specification means 2 uses the value that has been input as the first thickness.

After the diagnostician clicks a Confirm button with use of the mouse or the keyboard, the client PC 41 displays a screen having the three images represented by the image data sets generated from the second CT image data set CT2 on one of the high-definition LCD devices 42. The images to be displayed are similar to those shown in FIG. 8.

The diagnostician sets a starting position SP, an ending position EP, and a thickness in the screen being displayed, by using the mouse or the keyboard of the client PC 41. Based on the starting position SP and the ending position EP, the second cross section specification means 4 specifies three-dimensional inclination of the second cross section (that is, the second observation direction perpendicular to the second cross section) in the second region in a three-dimensional space relative to a photography direction, and a range in which the second cross section moves in the second observation direction. The second thickness specification means 5 uses the thickness that has been input as the second thickness.

After the diagnostician clicks the Confirm button for the second CT image CT2 by using the mouse or the keyboard of the client PC 41, the first cross section specification means 1, the first thickness specification means 2, the second cross section specification means 4, and the second thickness specification means 5 send the three-dimensional inclination of the first cross section, the moving range of the first cross section in the first observation direction, the first thickness, the three-dimensional inclination of the second cross section, the moving range of the second cross section in the second observation direction, and the second thickness to the image processing server 11 via the network 50.

Figure 9A:
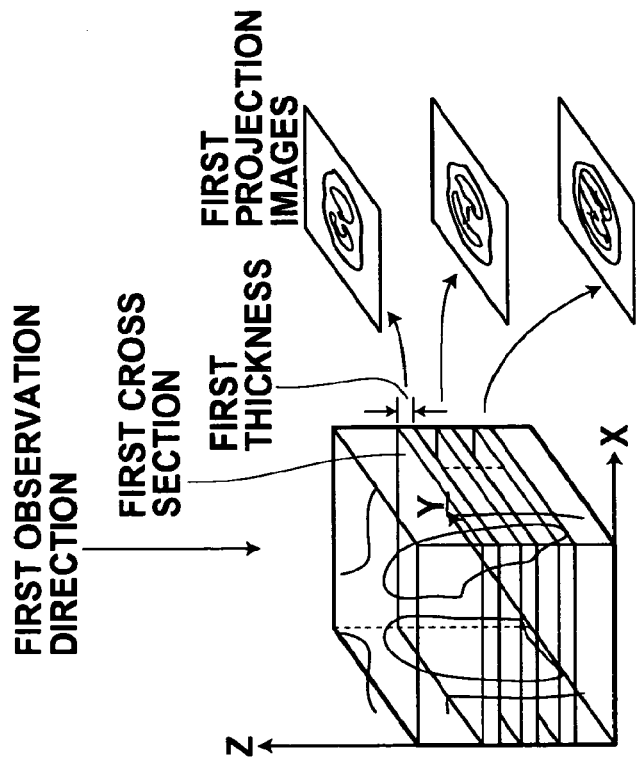

The image processing server 11 receives the three-dimensional inclination of the first cross section, the moving range of the first cross section in the first observation direction, the first thickness, the three-dimensional inclination of the second cross section, the moving range of the second cross section in the second observation direction, and the second thickness. Based on the three-dimensional inclination of the first cross section, the moving range of the first cross section in the first observation direction, and the first thickness that have been received, the first projection image generation means 3 divides the part specified by the starting position and the ending position of the first cross section into the regions having the first thickness in the first observation direction, and uses each of the regions as the first region in the first CT image CT1. For each of the regions specified as the first region in the above manner, the first projection image generation means 3 then finds an average of pixel values at points in a part of the first region along a line that has the same direction as the first observation direction and penetrates the first region. The pixel values at the points along the line may be found by interpolation processing using values of pixels around the line. In this manner, the first projection image is generated by projection of the pixels in the first region onto the plane perpendicular to the first observation direction (see FIG. 9A). The first projection images generated for all the regions are output as the first projection image data sets P1(i).

Based on the three-dimensional inclination of the second cross section, the moving range of the second cross section in the second observation direction, the second thickness, and the second CT image data set CT2 that have been received, the second projection image generation means 6 in the image processing server 11 specifies the regions each of which is used as the second region, and generates the second projection images for the respective regions in the same manner as the first projection image generation means 3. The second projection image data sets P2(j) are then output (see FIG. 9B).

The observation direction alignment processing unit 7a in the alignment processing means 7 of the image processing server 11 sequentially reads the first projection image data sets P1(i) and the second projection image data sets P2(j). Now, let P1(m) and P2(m) respectively denote the first projection image and the second projection image positioned $m^{th}$ from the first projection image including the first cross section at the starting position SP (denoted by P1(1)) and the second projection image including the second cross section at the starting position SP (denoted by P2(1)). The observation direction alignment processing unit 7a selects one of the second projection images (P2(n)) having the highest correlation of the pixel values among the second projection images P2(m) and P2(m±α) where α refers to a value satisfying $m-\alpha \leq n \leq m+\alpha$ and represents a predetermined range from the second projection image P2(m). FIG. 10 shows the case where α=1, 2 and correlation is compared between the pixel values in the first projection image P1(m) and the second projection images P2(m−2) to P2(m+2). The combination Q(m,n) of the first projection image P1(m) and the second projection image P2(n) corresponding thereto is found in this manner, and the remaining combinations can be determined automatically as Q(m−1, n−1), Q(m−2, n−2), . . . Q(m+1, n+1), Q(m+2, n+2) and so on. Alternatively, each of the combinations may be determined through comparison of correlation of the pixel values, in the same manner as for the combination Q(m,n).

Figure 11:
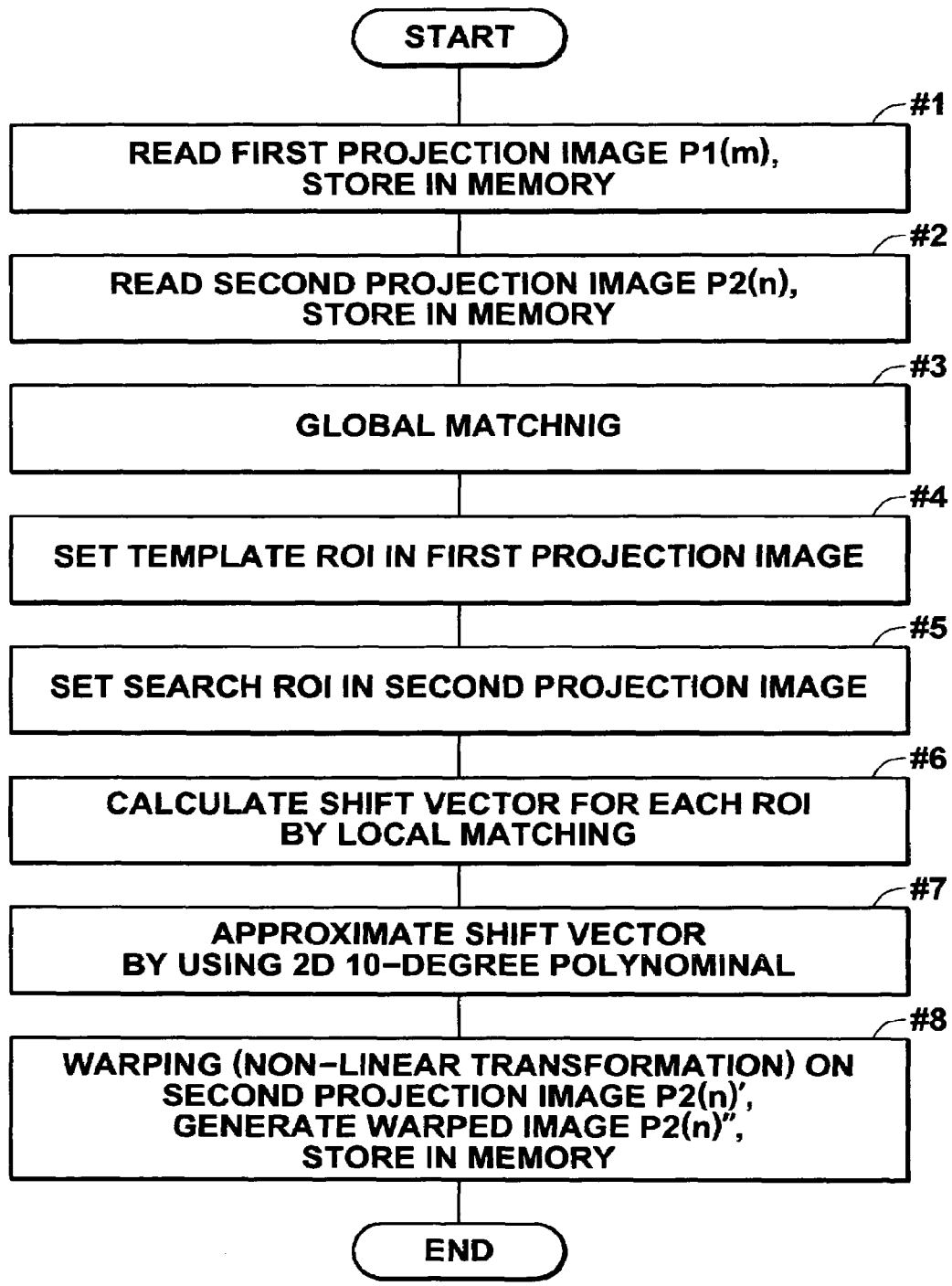
FIG. 11 is a flow chart showing a procedure carried out by a two-dimensional alignment processing unit.

A procedure carried out by the two-dimensional alignment processing unit 7b in the alignment means 7 of the image processing server 11 will be described next with reference to FIG. 11, for the combination Q(m,n) comprising the first projection image P1(m) and the second projection image P2(n).

In the two-dimensional alignment procedure, the first projection image P1(m) is read and stored in a first projection image memory (#1). The second projection image P2(n) is also read and stored in a second projection image memory (#2).

Overall alignment processing (referred to as global matching) is carried out (#3) between the first projection image P1(m) and the second projection image P2(n). More specifically, the second projection image P2(n) is subjected to affine transformation (rotation and translation) so that the second projection image P2(n) agrees with the first projection image P1(m). By this transformation, the second projection image P2(n) is transformed into a second projection image P2(n)', as shown in FIG. 12.

After completion of the global matching processing, local alignment processing (referred to as local matching processing) is carried out (#4~#7). The local matching processing will be described below in detail.

A region of interest (hereinafter referred to as a template ROI(T)) is set in the first projection image P1(m). As shown in FIG. 13, the template ROI(T) is represented initially by coordinates (x, y) of a pixel at the center thereof (#4). A search ROI (hereinafter referred to as a search ROI(R)) is also set (#5) in the transformed second projection image P2(n)'. The search ROI(R) has the same coordinates (x, y) of the center pixel as the corresponding template ROI(T), but has a larger area than the corresponding template ROI(T). In this example, the search ROI(R) has an area 4 times larger (that is, two times larger in vertical and horizontal directions, respectively) than the corresponding template ROI(T).

While the corresponding template ROI(T) is moved within the search ROI(R) that has been set in the transformed second projection image P2(n)', coordinates (x', y') of a position (the center of the moving ROI(T)) having the highest matching degree between the images P1(m) and P2(n)' is found (calculation of a shift vector for each ROI by local matching; #6). This procedure is repeated at various ROI (T) having the grid points in FIG. 13 as their centers. As an index of representing the matching degree, a least square or an index of cross-correlation may be used, for example.

Figure 14:
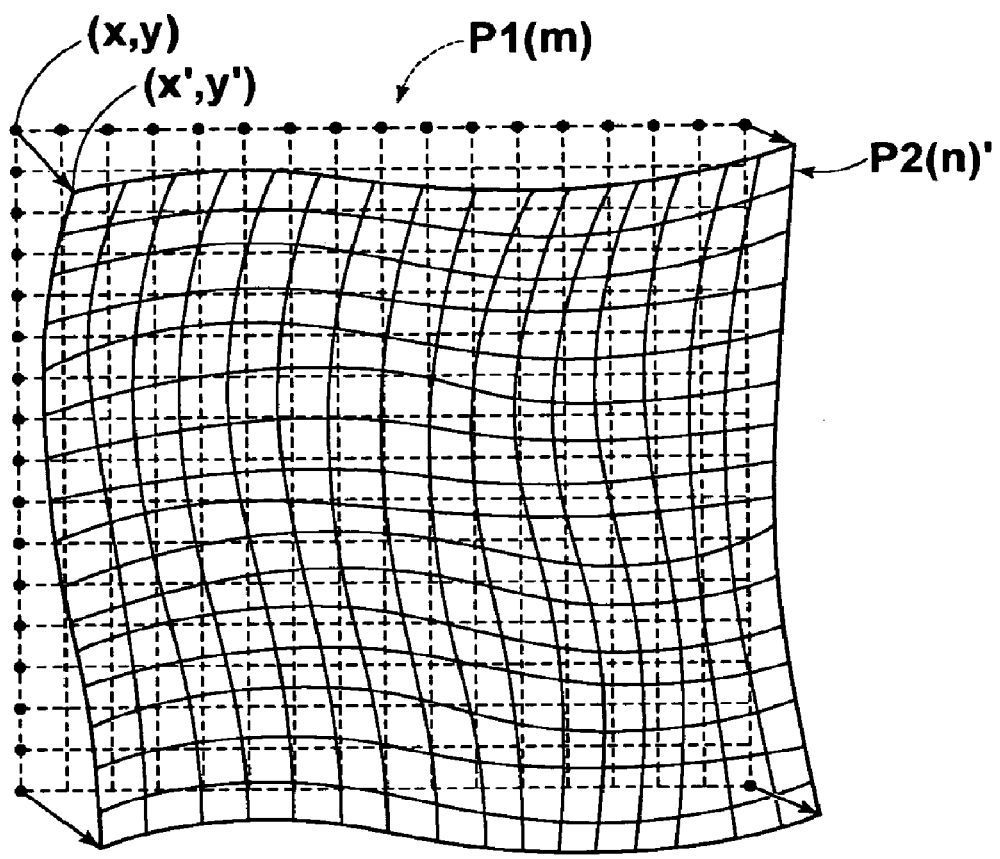
FIG. 14 shows how a center pixel shifts in each ROI found by the local matching processing by the two-dimensional alignment processing unit.

A shift vector represented by (Δx, Δy) found in the above manner (where Δx=x'−x, and Δy=y'−y) for the center pixel (x, y) in the search ROI(R) is as shown in the images P1(m) and P2(n)' in FIG. 14. In order to find shift vectors (Δx, Δy) for all the pixels in the transformed second projection image P2(n)' by using the shift vector (Δx, Δy) for the corresponding center pixel, approximation is carried out according to a two-dimensional fitting polynomial of degree 10 (#7). The transformed second projection image P2(n)' is then subjected to non-linear transformation (called warping) wherein each of the pixels (x, y) in the transformed second projection image P2(n)' is transformed based on the calculated shift vector (Δx, Δy). In this manner, a warped image (that is, the aligned second projection image P2(n)″) is generated and stored in a warped image memory (#8).

By the procedure described above, the subject in the second projection image P2(n) has been aligned to the subject in the first projection image P1(m), and the warped image P2(n)″ is generated. The aligned second projection image data set P2(n)″ is then output. In FIG. 7, the combination Q(m,n)' is a combination of the projection images P1(m) and P2(n)″ having been subjected to the two-dimensional alignment processing.

The same procedure is carried out for the remaining combinations determined by the observation direction alignment processing unit 7a.

The subtraction processing unit 8a in the superposed subtraction image generation means 8 reads the first projection image data set P1(m) and the aligned second projection image data set P2(n)″, and generates a subtraction image R(K) by carrying out subtraction processing on the pixels corresponding to each other in the images represented by the two image data sets. The subtraction processing unit 8a then outputs the subtraction image data set R(k) representing the subtraction image. The index k refers to the $k^{th}$ combination determined by the observation direction alignment processing unit 7a. The subtraction processing unit 8a carries out the same processing on the remaining combinations after the two-dimensional alignment processing, and generates the subtraction image data sets R(k).

The superposition processing unit 8b reads all the subtraction image data sets R(k), and carries out averaging processing thereon. The superposition processing unit 8b then generates an averaged subtraction image as a superposed subtraction image S, and outputs the superposed subtraction image data set S representing the superposed subtraction image. The superposed subtraction image data set S is sent from the image processing server 11 to the client PC 41 in the image display system 40 via the network 50.

In the client PC 41, the image display means 93 displays the superposed subtraction image S on one of the high-definition LCD devices 42, based on the superposed subtraction image data set S. The superposed subtraction image S is provided to the diagnostician for comparative image reading.

As has been described above, according to the image interpretation aiding apparatus 101 in the first embodiment of the present invention, the first and second projection images are generated by projecting the pixels in the regions specified by the predetermined cross sections and the predetermined thicknesses forming the observation target in the first and second CT images CT1 and CT2 obtained by photography of the same subject at different times. The first and second projection images corresponding to each other are subjected to the alignment processing and the subtraction image generation processing, and the superposed subtraction image is generated by superposing the subtraction images. Therefore, regardless of a three-dimensional positioning change or the like in the subject, accuracy of the alignment processing can be improved for the observation target, and artifacts in the subtraction images can be suppressed (see FIGS. 3 and 4). Consequently, the diagnostician can carry out the comparative image reading with high accuracy, and the image reading can be carried out effectively.

In this embodiment, the image display means 93 displays the superposed subtraction image. However, other images may also be displayed at the same time. For example, in the image processing server 11, a first observation target image may be generated by projecting pixels in the part in the first CT image data set CT1 specified by the starting and ending positions SP and EP of the first cross section onto a plane parallel to the first cross section so that a first observation target image data set is output. In this case, a second observation target image data set is also output by generation of a second observation target image through projection of pixels in the part in the second CT image data set CT2 specified by the starting and ending positions SP and EP of the second cross section onto a plane parallel to the second cross section. The observation target image data sets are sent from the image processing server 11 to the client PC 41 in the image display system 40 via the network 50, and the image display means 93 of the client PC 41 displays the two observation target images on two of the high-definition LCD devices 42 (see FIG. 15), based on the two observation target image data sets. In this manner, the diagnostician can view the two observation target images wherein the entire observation target is projected, together with the superposed subtraction image as the subtraction image between the two observation target images. Consequently, if the diagnostician finds a part representing an interval change in the superposed subtraction image, the diagnostician can confirm the part in the original projection images, which improves diagnostic efficiency. Furthermore, the image processing server 11 or the large-capacity external storage 32 of the image management system 30 may temporarily store at least one of the combinations of the first projection image data set P1(m) and the aligned second projection image data set P2(n)″. In this case, the client PC 41 receives the stored image data sets via the network 50, and the image display means 93 displays the first projection image P1(m) and the corresponding aligned second projection image P2(n)" on the high-definition LCD devices 42, based on the image data sets. Furthermore, the image processing server 11 or the large-capacity external storage 32 may store at least one of the subtraction image data sets R(k) before the superposition processing so that the client PC 41 can receive the subtraction image data set or sets via the network 50. The image display means 93 then displays the subtraction image or images R(k) on the high-definition LCD devices 42, based on the subtraction image data set or sets.

An image interpretation aiding apparatus 102 of a second embodiment of the present invention will be described next. The image interpretation aiding apparatus 102 generates the projection images by projecting the pixels in the regions specified by the cross sections and the thicknesses in the two CT images representing the same subject but photographed at different times. The image interpretation aiding apparatus 102 then carries out alignment processing on lung fields in the projection images corresponding to each other, and carries out superposition processing on the projection images of the respective CT images having been subjected to the alignment processing. The image interpretation aiding apparatus 102 then generates the superposed subtraction image, based on a difference between the two projection images having been subjected to the superposition processing.

Figure 16:
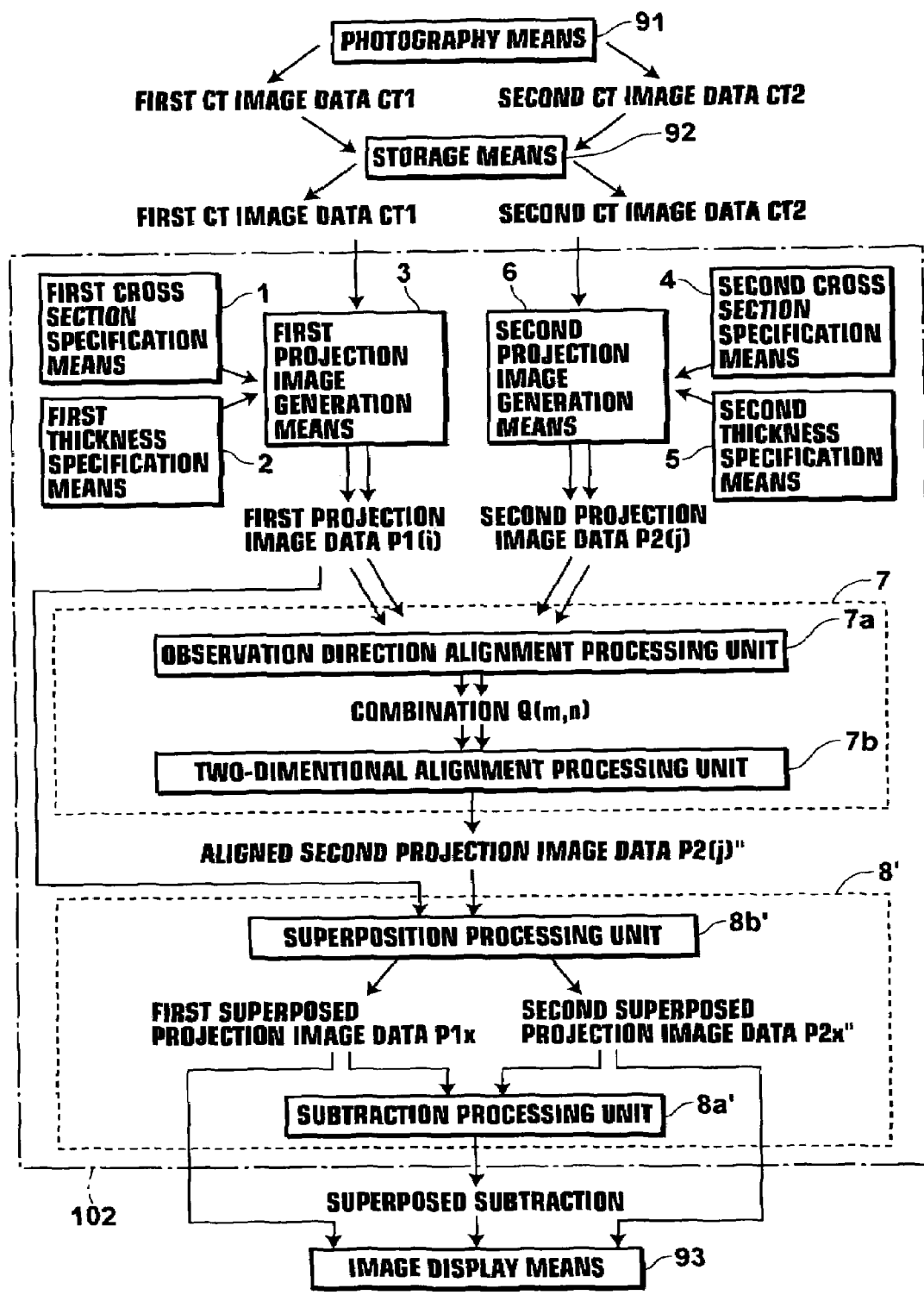
FIG. 16 is a block diagram showing the configuration of an image interpretation aiding apparatus and peripheral systems and flows of data in a second embodiment of the present invention

FIG. 16 is a block diagram showing a configuration of the image interpretation aiding apparatus 102 and peripheral systems, and flows of data. As shown in FIG. 16, the image interpretation aiding apparatus 102 has superposed subtraction image generation means 8' replacing the superposed subtraction image generation means 8 in the image interpretationaiding apparatus 101, which is a difference from the image interpretation aiding apparatus 101. The superposed subtraction image generation means 8' comprises a superposition processing unit 8b' and a subtraction processing unit 8a'. The superposition processing unit 8b' generates a first superposed projection image P1x and a second superposed projection image P2x" by respectively superposing the first projection images P1(i) and the aligned second projection images P2(j)". The subtraction processing unit 8a' generates the superposed subtraction image by finding the difference between the first superposed projection image P1x and the second superposed projection image P2x", and outputs the superposed subtraction image data set S. Hereinafter, a procedure carried out in the image interpretation aiding system 102 and the peripheral systems will be described next, mainly on the difference from the image interpretation aiding apparatus 101.

In the image interpretation aiding apparatus 102, the alignment processing means 7 generates the aligned second projection image P2(n)" by aligning the subject in the second projection image P2(n) to the subject in the first projection image P1(m) in the same manner as the image interpretation aiding apparatus 101. The alignment processing means 7 carries out this alignment processing for all of the first projection images P1(i) and the second projection images P2(j), and outputs the aligned second projection image data sets P2(n)".

The superposition processing unit 8b' in the superposed subtraction image generation means 8' reads all the first projection image data sets P1(i), and carries out averaging processing thereon for generating the first superposed projection image P1x. The superposition processing unit 8b' outputs a first superposed projection image data set P1x. The superposition processing unit 8b' also reads all the aligned second projection image data sets P2(j)", and carries out averaging processing thereon for generating the second superposed projection image P2x". The superposition processing unit 8b' then outputs a second superposed projection image data set P2x".

The subtraction processing unit 8a' reads the first superposed projection image data set P1x and the second superposed projection image data set P2x", and carries out subtraction processing between pixels corresponding to each other therein. The subtraction processing unit 8a' then outputs the superposed subtraction image data set S representing the superposed subtraction image.

In the image interpretation aiding apparatus 102, the superposed subtraction image data set S, the first superposed projection image data set P1x, the second superposed projection image data set P2x" are sent from the image processing server 11 to the client PC 41 in the image display system 40 via the network 50.

In the client PC41, the image display means 93 displays the first superposed projection image P1x, the second superposed projection image P2x", and the superposed subtraction image S on the respective high-definition LCD devices 42, based on the image data sets that have been received. The images are then provided to the diagnostician for comparative image reading.

As has been described above, according to the image interpretation aiding apparatus 102 of the second embodiment of the present invention, the same effect as the image interpretation aiding apparatus 101 of the first embodiment can be obtained. In addition, the first superposed projection image P1x and the second superposed projection image P2x" are obtained by respectively superposing the first projection images P1(i) and the aligned second projection images P2(j)". The superposed subtraction image S is then generated by finding the difference between the first superposed projection image P1x and the second superposed projection image P2x". By providing the first superposed projection image P1x, the second superposed projection image P2x", and the superposed subtraction image S for comparative image reading, image reading can be carried out on the two projection images having been subjected to the alignment processing with high accuracy regarding the observation target and on the subtraction image. Therefore, the comparative image reading can be carried out more efficiently and more accurately.

Modifications to the two embodiments of the present invention within the scope of the present invention will be described next.

As shown in FIG. 6, the functions of these embodiments are installed separately in the respective systems. However, all or a part of the functions may be installed in one computer, which is effective for a small-sized system.

In the embodiments described above, the observation direction is the photography direction (the axial direction) However, the observation direction is not necessarily limited to the axial direction, and the frontal direction, the side direction or other directions may be used. For example, by selecting an "Oblique Direction Display" box in the right of the screen shown in FIG. 17, cross sectional images viewed from any arbitrary direction other than the axial, frontal and side directions may also be displayed. By adjusting three-dimensional inclination of the cross sectional images with inclination adjustment buttons, the diagnostician may specify the starting position SP and the ending position EP. In this case, information representing how the inclination adjustment buttons are used at the time of inclination adjustment is sent from the image processing server 11 via the network 50, and the image processing server 11 reconstructs the cross sectional images according to the information based on an MPR method. The reconstructed cross sectional images are sent to the client PC 41 via the network 50, and displayed on one of the high-definition LCD devices 42. If the first and second cross sections are specified to be perpendicular to the observation directions desired by the diagnostician as in this case, the subtraction images can be generated from the cross sections useful for observation of an interval change of a disease or the like, which improves diagnostic efficiency for the diagnostician.

In the above-described embodiments, the second cross section and the second thickness are specified after the first cross section and the first thickness have been specified. However, when the same screen as in FIG. 8 is displayed based on the second CT image data set CT2, the three-dimensional inclination of the first cross section that has been set for the first CT image CT1 may be displayed in the screen together with the starting position SP and the ending position EP of the first cross section corresponding to the moving range in the first observation direction, and the same value as the first thickness may also be displayed in the box for the thickness of the regions. Furthermore, without display of the screen for setting the second cross section and the second thickness, the second cross section specification means 4 may automatically determine the three-dimensional inclination of the second cross section and the moving range of the second cross section in the second observation direction, in consideration of the three-dimensional inclination of the first cross section and the moving range of the first cross section in the first observation direction that have been set for the first CT image CT1. The second thickness specification means 5 may also use the value of the first thickness as the value of the second thickness. In this manner, the diagnostician can easily specify or does not need to specify the second cross section and the second thickness, which improves diagnostic efficiency. The phrase "in consideration" refers to having the same vector in the three-dimensional space relative to the photography direction of the first CT image CT1, and does not refer to specific three-dimensional inclination or position relative to the subject. Therefore, as shown in FIG. 9, even in the case where the three-dimensional inclination of the second cross section is specified by the same vector that represents the three-dimensional inclination of the first cross section in the three-dimensional space relative to the photography direction of the first CT image CT1, if three-dimensional positioning of the subject in the first CT image CT1 is different from that of the second CT image CT2 at the time of photography thereof, the three-dimensional inclination (the observation directions) of the cross sections relative to the subject may not be the same between the two images. However, in the present invention, the projection image generation, the alignment processing, and the subtraction image generation are carried out for the regions in the part including the observation target, and superposition of the subtraction images is carried out on the subtraction images in the first embodiment. Therefore, alignment accuracy improvement and artifact reduction can be achieved.

Figure 17:
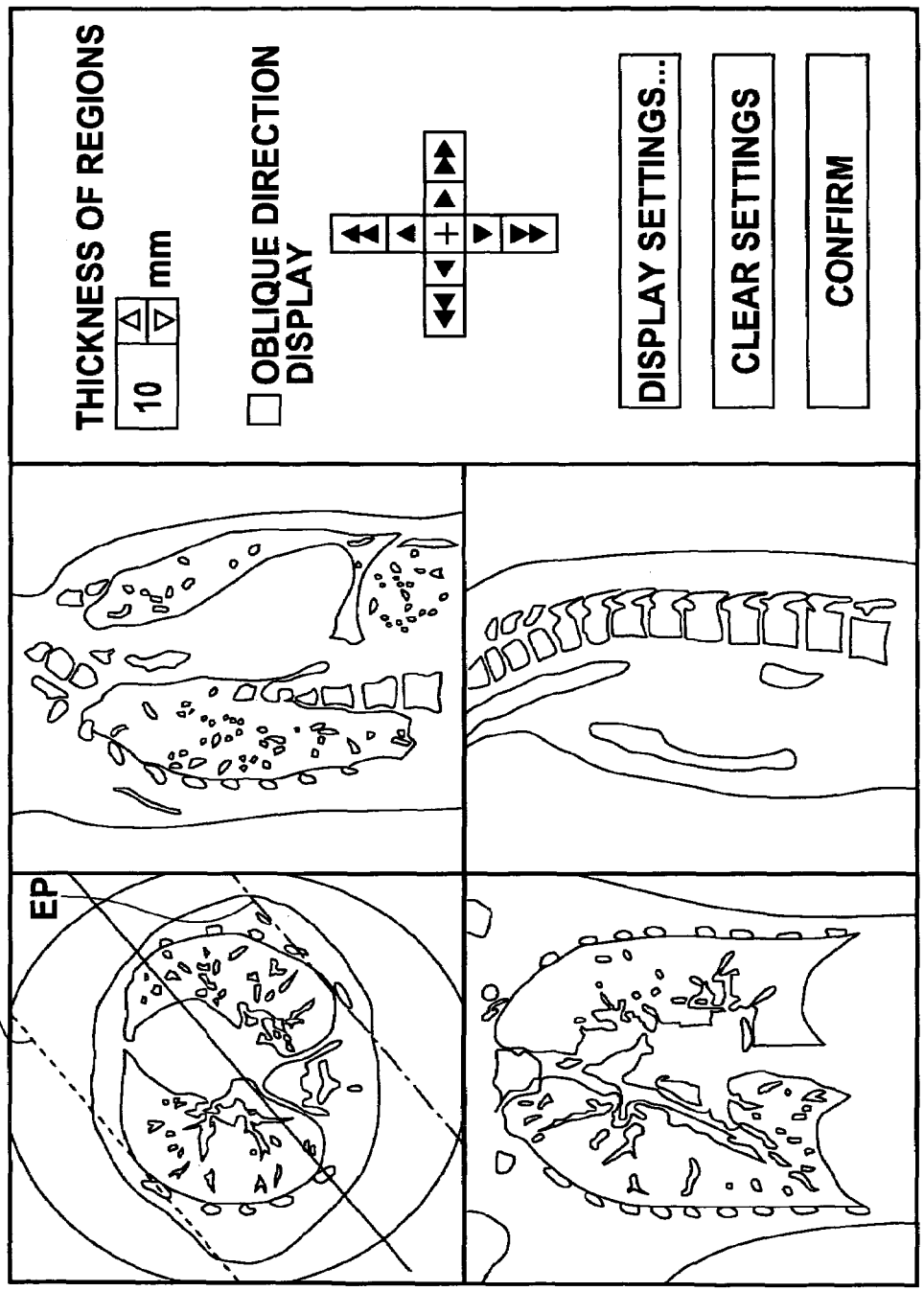
FIG. 17 shows an example of a screen used in the case where the first and second cross sections-are specified in an oblique direction.

In the embodiments described above, it is preferable for the photography directions to be substantially the same between the first CT image CT1 and the second CT image CT2 to a degree that enables comparative image reading. However, in the case where the photography directions are different between the two images, the two images may be subjected to overall alignment processing. More specifically, the following methods can be used therefor:

(1) For at least one of the first and second CT images CT1 and CT2, the "Oblique Direction Display" box is selected as shown in FIG. 17. The diagnostician then operates the client PC 41 for display of the cross sections of the CT image viewed in substantially the same direction as the other CT image. The diagnostician then sets the first and second cross sections to cause the three-dimensional inclination of the first cross section to substantially agree with that of the second cross section.

Figure 18:
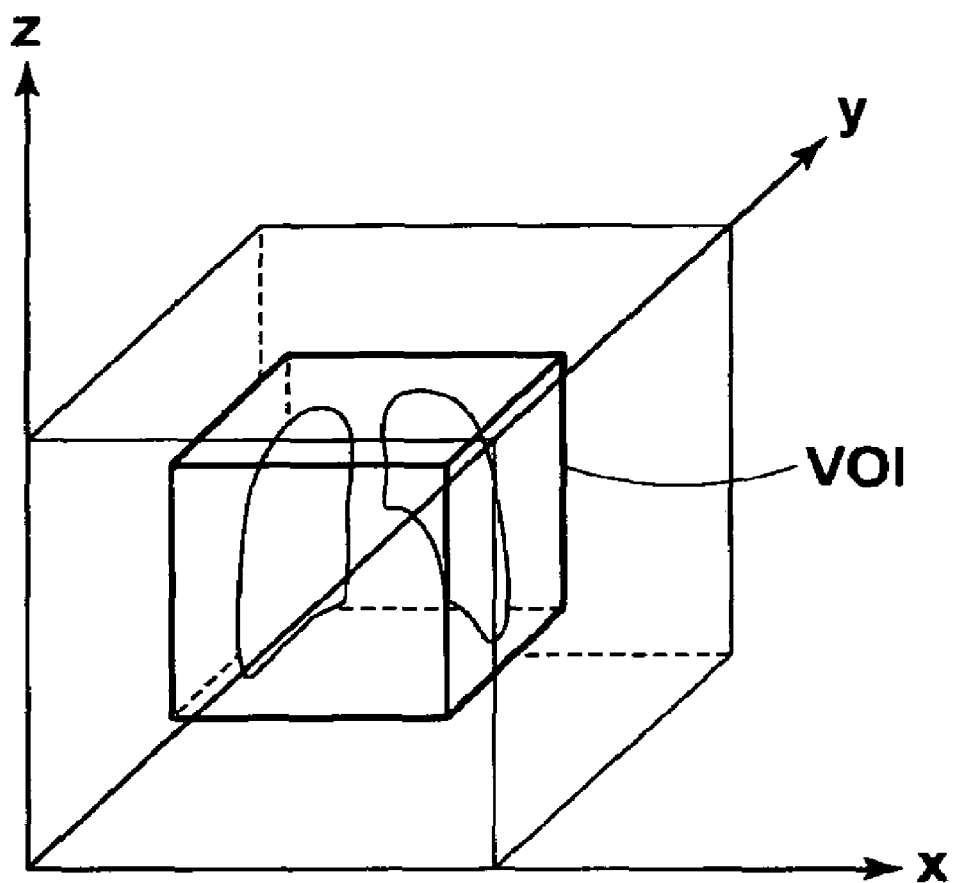
FIG. 18 shows a volume of interest (VOI) including a rib cage in a chest CT image.

(2) The diagnostician cuts a volume of interest (referred to as VOI in FIG. 18) including a rib cage from the first CT image CT1, and the image processing server 11 translates and rotates the volume in the second CT image CT2 for finding magnitude of displacement and rotation of the volume in the case where pixel values of the VOI show the highest correlation with the corresponding pixel values in the second CT image CT2. The pixels in one of the CT images are then translated and rotated according to the magnitude of displacement and rotation for overall alignment of the two images. After the alignment, the first and second cross sections are specified in the same manner as the embodiments described above.

(3) The image processing server 11 automatically extracts upper and lower lung fields by carrying out rib cage recognition processing (see Japanese Unexamined Patent Publications Nos. 2002-109548 and 2002-109550, for example) in the same manner as for a simple chest X-ray image on a projection image generated by projection of a part in the first CT image CT1 specified by a cross section viewed from the frontal direction of the subject and a thickness of the human body measured in the direction from the front to the rear of the body onto a plane parallel to the cross section. The same processing described in (2) above is carried out on a volume specified by the extracted upper and lower lung fields and the thickness in the frontal-rear direction of the human body.

In this manner, the three-dimensional inclination (that is, the first observation direction) of the first cross section can agree to that of the second cross section to the degree enabling comparative image reading. In this manner, diagnostic efficiency can be improved for the diagnostician.

In the embodiments described above, after the diagnostician inputs the values of thicknesses, the first and second thickness specification means 2 and 5 may examine the values that have been input. In this case, a warning message may be displayed if the values are equal to smaller than the slice thicknesses for the first and second CT images, respectively. Alternatively, the slice thicknesses may be displayed in advance so that the diagnostician is prompted to input values larger than the displayed values. In this manner, the first and second thicknesses can be larger than the slice thicknesses for the first and second CT images respectively, and correspondence of the structural characteristic in the projection images can be prevented from being lacked due to a change in three-dimensional positioning of the subject (see FIG. 5). Consequently, accuracy of alignment can be improved more than in the case of alignment processing on projection images generated by projection of regions having thicknesses equal to or smaller than the slice thicknesses.

In the embodiments described above, the observation direction alignment processing unit 7a automatically selects the second projection images respectively corresponding to the first projection images. However, a screen may be used for allowing the diagnostician to determine correspondence between the first and second projection images while viewing the first and second projection images. For example, the first projection images may be displayed sequentially in the upper part of the screen as shown in FIG. 10 while the second projection images are displayed sequentially in the lower part thereof. In this manner, the diagnostician can determine the correspondence between the first and second projection images by using the mouse or the like of the client PC 41.

What is claimed is:

1. An image interpretation aiding method comprising the steps of:
generating first projection images of a first region in a first three-dimensional image representing a subject by projecting, onto a plane perpendicular to a first observation direction to the subject in the first three-dimensional image, pixels in the first region specified by a first cross section perpendicular to the first observation direction and a first thickness equal to a first pitch, which is a thickness from the first cross section in the first observation direction, while moving a position of the first cross section in the first observation direction by the first pitch;
generating second projection images of a second region in a second three-dimensional image representing the subject obtained at a time different from the first three-dimensional image by projecting, onto a plane perpendicular to a second observation direction to the subject in the second three-dimensional image, pixels in the second region specified by a second cross section perpendicular to the second observation direction and a second thickness equal to a second pitch, which is a thickness from the second cross section in the second observation direction, while moving a position of the second cross section in the second observation direction by the second pitch;
carrying out alignment processing for aligning the subject in each of combinations of the first projection images and the second projection images corresponding to each other; and
generating a superposed subtraction image based on a difference between all the first projection images and all the second projection images having been subjected to the alignment processing.

2. The image interpretation aiding method according to claim 1, the step of generating the superposed subtraction image comprising the steps of:
generating subtraction images from a difference in each of the combinations of the first projection images and the second projection images having been subjected to the alignment processing; and
generating the superposed subtraction image by superposing the subtraction images.

3. The image interpretation aiding method according to claim 1, the step of generating the superposed subtraction image comprising the steps of:
generating a first superposed projection image by superposing the first projection images having been subjected to the alignment processing;
generating a second superposed projection image by superposing the second projection images having been subjected to the alignment processing; and
generating the superposed subtraction image by finding a difference between the first superposed projection image and the second superposed projection image.

4. The image interpretation aiding method according to claim 1,
the first three-dimensional image and the second three-dimensional image respectively comprising cross sectional images representing slice regions generated by sequentially slicing the subject according to slice thicknesses predetermined respectively for the first three-dimensional image and the second three-dimensional image,
the first thickness being larger than the predetermined slice thickness for the first three-dimensional image, and
the second thickness being larger than the predetermined slice thickness for the second three-dimensional image.

5. The image interpretation aiding method according to claim 1, wherein the alignment processing comprises the steps of:
observation direction alignment processing for determining the combinations of the first projection images and the second projection images corresponding to each other by respectively selecting the second projection images having the highest correlation of pixel values with the respective first projection images; and
two-dimensional alignment processing comprising global matching, local matching, and warping,
the global matching being overall linear alignment processing for detecting an overall amount of rotation and/or translation between the two projection images comprising each of the combinations,
the local matching being local non-linear alignment processing for detecting shift vectors between corresponding local areas in the two projection images and for determining shift vectors between each pair of corresponding pixels in the two projection images based on the shift vectors between the local areas, and
the warping being processing for nonlinearly transforming one of the two projection images to the other one of the two projection images based on the shift vectors between the pixels.

6. The image interpretation aiding method according to claim 1, further comprising the steps of:
setting a three-dimensional volume of interest in the first three-dimensional image;
calculating magnitude of displacement and rotation of the volume in the case where pixel values of the volume show the highest correlation with pixel values of a corresponding volume in the second three-dimensional image while translating and rotating the volume in the second three-dimensional image; and
carrying out overall alignment between the two three-dimensional images by translating and rotating pixels in one of the two three-dimensional images based on the magnitude of displacement and rotation, wherein
the steps of generating the first projection images and the second projection images are carried out after the overall alignment.

7. An image interpretation aiding apparatus comprising:
first cross section specification means for specifying a first cross section perpendicular to a first observation direction to a subject in a first three-dimensional image representing the subject;
first thickness specification means for specifying a first thickness from the first cross section in the first observation direction;
first projection image generation means for generating first projection images of a first region in the first three-dimensional image by projecting, onto a plane perpendicular to the first observation direction, pixels in the first region specified by the first cross section and the first thickness while moving a position of the first cross section in the first observation direction by a pitch equal to the first thickness;
second cross section specification means for specifying a second cross section perpendicular to a second observation direction to the same subject in a second three-dimensional image representing the subject and obtained at a time different from the first three-dimensional image;

second thickness specification means for specifying a second thickness from the second cross section in the second observation direction;

second projection image generation means for generating second projection images of a second region in the second three-dimensional image by projecting, onto a plane perpendicular to the second observation direction, pixels in the second region specified by the second cross section and the second thickness while moving a position of the second cross section in the second observation direction by a pitch equal to the second thickness;

alignment processing means for carrying out alignment processing on the subject in each of combinations of the first projection images and the second projection images corresponding to each other; and superposed subtraction image generation means for generating a superposed subtraction image based on a difference between all the first projection images and all the second projection images having been subjected to the alignment processing.

8. The image interpretation aiding apparatus according to claim 7, wherein the superposed subtraction image generation means generates:

subtraction images based on a difference in each of the combinations of the first projection images and the corresponding second projection images having been subjected to the alignment processing, and the superposed subtraction image by superposing the subtraction images.

9. The image interpretation aiding apparatus according to claim 7, wherein the superposed subtraction image generation means generates:

a first superposed projection image by superposing the first projection images having been subjected to the alignment processing, a second superposed projection image by superposing the second projection images having been subjected to the alignment processing, and the superposed subtraction image by finding a difference between the first superposed projection image and the second superposed projection image.

10. The image interpretation aiding apparatus according to claim 7, the first three-dimensional image and the second three-dimensional image respectively comprising cross sectional images representing slice regions generated by sequentially slicing the subject according to slice thicknesses predetermined respectively for the first three-dimensional image and the second three-dimensional image, wherein the first thickness specification means and the second thickness specification means respectively examine values specified respectively as the first thickness and the second thickness and respectively display a warning message in the case where the value specified as the first thickness is not larger than the predetermined slice thickness for the first three-dimensional image and in the case where the value specified as the second thickness is not larger than the predetermined slice thickness for the second three-dimensional image.

11. The image interpretation aiding apparatus according to claim 7, the first three-dimensional image and the second three-dimensional image respectively comprising cross sectional images representing slice regions generated by sequentially slicing the subject according to slice thicknesses predetermined respectively for the first three-dimensional image and the second three-dimensional image, wherein the first thickness specification means and the second thickness specification means respectively display the predetermined slice thickness for the first three-dimensional image and the predetermined slice thickness for the second three-dimensional image in advance for prompting specification of values larger than the displayed slice thicknesses.

12. The image interpretation aiding apparatus according to claim 7, wherein the second cross section specification means specifies a cross section corresponding to the first cross section in the second three-dimensional image as the second cross section, and the second thickness specification means specifies a value that is the same as the first thickness as the second thickness.

13. The image interpretation aiding apparatus according to claim 7, wherein the alignment processing means comprises:

an observation direction alignment processing unit for determining the combinations of the first projection images and the second projection images corresponding to each other by respectively selecting the second projection images having the highest correlation of pixel values with the respective first projection images; and a two-dimensional alignment processing unit for carrying out global matching, local matching, and warping, the global matching being overall linear alignment processing for detecting an overall amount of rotation and/or translation between the two projection images comprising each of the combinations, the local matching being local non-linear alignment processing for detecting shift vectors between corresponding local areas in the two projection images and for determining shift vectors between each pair of corresponding pixels in the two projection images based on the shift vectors between the local areas, and the warping being a process for nonlinearly transforming one of the two projection images to the other one of the two projection images based on the shift vectors between the pixels.

14. The image interpretation aiding apparatus according to claim 7, the image interpretation aiding apparatus further comprising:

means for setting a three-dimensional volume of interest in the first thee-dimensional image, for calculating magnitude of displacement and rotation of the volume in the case where pixel values of the volume show the highest correlation with pixel values of a corresponding volume in the second three-dimensional image while translating and rotating the volume in the second three-dimensional image, and for carrying out overall alignment between the two three-dimensional images by translating and rotating the pixels in one of the two three-dimensional images based on the magnitude of displacement and rotation, wherein the first cross section specification means and the second cross section specification means respectively specify the first cross section and the second cross section after the overall alignment.

15. A computer-readable recording medium storing an image interpretation aiding program for causing a computer to function as:

first cross section specification means for specifying a first cross section perpendicular to a first observation direction to a subject in a first three-dimensional image representing the subject;

first thickness specification means for specifying a first thickness from the first cross section in the first observation direction;

first projection image generation means for generating first projection images of a first region in the first three-dimensional image by projecting, onto a plane perpendicular to the first observation direction, pixels in the first region specified by the first cross section and the first thickness while moving a position of the first cross section in the first observation direction by a pitch equal to the first thickness;

second cross section specification means for specifying a second cross section perpendicular to a second observation direction to the same subject in a second three-dimensional image representing the subject and obtained at a time different from the first three-dimensional image;

second thickness specification means for specifying a second thickness from the second cross section in the second observation direction;

second projection image generation means for generating second projection images of a second region in the second three-dimensional image by projecting, onto a plane perpendicular to the second observation direction, pixels in the second region specified by the second cross section and the second thickness while moving a position of the second cross section in the second observation direction by a pitch equal to the second thickness;

alignment processing means for carrying out alignment processing on the subject in each of combinations of the first projection images and the second projection images corresponding to each other; and superposed subtraction image generation means for generating a superposed subtraction image based on a difference between all the first projection images and the second projection images having been subjected to the alignment processing.

16. A computer-readable recording medium storing the image interpretation aiding program of claim 15, the image interpretation aiding program causing the computer to cause the superposed subtraction image generation means to generate:

subtraction images based on a difference in each of the combinations of the first projection images and the corresponding second projection images having been subjected to the alignment processing, and the superposed subtraction image by superposing the subtraction images.

17. A computer-readable recording medium storing the image interpretation aiding program of claim 15, the image interpretation aiding program causing the computer to cause the superposed subtraction image generation means to generate:

a first superposed projection image by superposing the first projection images having been subjected to the alignment processing, a second superposed projection image by superposing the second projection images having been subjected to the alignment processing, and the superposed subtraction image by finding a difference between the first superposed projection image and the second superposed projection image.

18. A computer-readable recording medium storing the image interpretation aiding program of claim 15, the first three-dimensional image and the second three-dimensional image respectively comprising cross sectional images representing slice regions generated by sequentially slicing the subject according to slice thicknesses predetermined respectively for the first three-dimensional image and the second three-dimensional image, and the image interpretation aiding program causing the computer to cause the first thickness specification means and the second thickness specification means to respectively examine values specified as the first thickness and the second thickness and to respectively display a warning message in the case where the value specified as the first thickness is not larger than the predetermined slice thickness for the first three-dimensional image and in the case where the value specified as the second thickness is not larger than the predetermined slice thickness for the second three-dimensional image.

19. A computer-readable recording medium storing the image interpretation aiding program of claim 15, the first three-dimensional image and the second three-dimensional image respectively comprising cross sectional images representing slice regions generated by sequentially slicing the subject according to slice thicknesses predetermined respectively for the first three-dimensional image and the second three-dimensional image, and the image interpretation aiding program causing the computer to cause the first thickness specification means and the second thickness specification means to respectively display the predetermined slice thickness for the first three-dimensional image and the predetermined slice thickness for the second three-dimensional image in advance for prompting specification of values larger than the displayed slice thicknesses.

20. A computer-readable recording medium storing the image interpretation aiding program of claim 15, wherein the image interpretation aiding program causes the computer to cause:

the second cross section specification means to specify a cross section corresponding to the first cross section in the second three-dimensional image as the second cross section, and the second thickness specification means to specify a value that is the same as the first thickness as the second thickness.

21. A computer-readable recording medium storing the image interpretation aiding program of claim 15, wherein the image interpretation aiding program causes the computer to cause the alignment processing means to function as:

an observation direction alignment processing unit for determining the combinations of the first projection images and the second projection images corresponding to each other by respectively selecting the second projection images having the highest correlation of pixel values with the respective first projection images; and a two-dimensional alignment processing unit for carrying out global matching, local matching, and warping, the global matching being overall linear alignment processing for detecting an overall amount of rotation and/or translation between the two projection images comprising each of the combinations, the local matching being local non-linear alignment processing for detecting shift vectors between corresponding local areas in the two projection images and for determining shift vectors between each pair of corresponding pixels in the two projection images based on the shift vectors between the local areas, and the warping being a process for nonlinearly transforming one of the two projection images to the other one of the two projection images based on the shift vectors between the pixels.

22. A computer-readable recording medium storing the image interpretation aiding program of claim 15, the image interpretation aiding program further causing the computer to further function as:

means for setting a three-dimensional volume of interest in the first three-dimensional image, for calculating magnitude of displacement and rotation of the volume in the case where pixel values of the volume show the highest correlation with pixel values of a corresponding volume in the second three-dimensional image while translating and rotating the volume in the second three-dimensional image, and for carrying out overall alignment between the two three-dimensional images by translating and rotating the pixels in one of the two three-dimensional images based on the magnitude of displacement and rotation, wherein the first cross section specification means and the second cross section specification means specify the first cross section and the second cross section after the overall alignment.

23. The image interpretation aiding method according to claim 1, wherein said superposed subtraction image is the same size as the first and second projection images, and the first projection images, the second projection images, and the superposed subtraction image are digital image data.

* * * * *